US012727739B2

(12) United States Patent
Peleg et al.

(10) Patent No.: US 12,727,739 B2
(45) Date of Patent: Sep. 8, 2026

(54) ESTIMATING THE ADEQUACY OF A PROCEDURE

(71) Applicant: Given Imaging LTD., Yoqneam (IL)

(72) Inventors: Dori Peleg, Kiryat Bialik (IL); Dov Eilot, Yokneam (IL); Yossi Tsadok, Pardes Hanna-Karkur (IL)

(73) Assignee: Given Imaging LTD., Yoqneam (IL)

( * ) Notice: Subject to any disclaimer, the term of this patent is extended or adjusted under 35 U.S.C. 154(b) by 562 days.

(21) Appl. No.: 18/021,030

(22) PCT Filed: Sep. 1, 2021

(86) PCT No.: PCT/IL2021/051074
§ 371 (c)(1),
(2) Date: Feb. 13, 2023

(87) PCT Pub. No.: WO2022/054043
PCT Pub. Date: Mar. 17, 2022

(65) Prior Publication Data

US 2023/0320562 A1 Oct. 12, 2023

Related U.S. Application Data

(60) Provisional application No. 63/228,937, filed on Aug. 3, 2021, provisional application No. 63/075,778, filed on Sep. 8, 2020.

(51) Int. Cl.
*A61B 1/00* (2006.01)
*A61B 1/04* (2006.01)
(Continued)

(52) U.S. Cl.
CPC .......... *A61B 1/00009* (2013.01); *A61B 1/041* (2013.01); *A61B 1/2736* (2013.01); *G16H 30/00* (2018.01)

(58) Field of Classification Search
CPC ..... A61B 1/00009; G16H 30/00; G16H 40/60
See application file for complete search history.

(56) References Cited

U.S. PATENT DOCUMENTS 8,691,291 B1 * 4/2014 Arya .......................... A61P 1/10 424/722
8,792,691 B1 * 7/2014 Rozenfeld ............ G11B 27/034 382/128
(Continued)

FOREIGN PATENT DOCUMENTS

CN 109480746 A 3/2019
JP 2020078539 A 5/2020
(Continued)

OTHER PUBLICATIONS

International Search Report and Written Opinion of the International Searching Authority issued in corresponding application PCT/IL2021/051074 mailed Dec. 2, 2021 (10 pages).
(Continued)

*Primary Examiner* — Anh Tuan T Nguyen
*Assistant Examiner* — Jae Woo
(74) *Attorney, Agent, or Firm* — Carter, DeLuca & Farrell, LLP

(57) ABSTRACT

A computer-implemented method for estimating adequacy of a capsule endoscopy (CE) procedure includes: accessing a plurality of images of at least a portion of a gastrointestinal tract (GIT) captured by a CE imaging device during a CE procedure; accessing a plurality of characteristic measures associated with the plurality of images; determining an adequacy measure for the CE procedure based on the plurality of characteristic measures, where the adequacy measure provides a measure of whether an imaging coverage provided by the plurality of images was adequate to capture an event of interest in the at least the portion of the GIT, whether or not such an event of interest actually exists
(Continued)

in the at least the portion of the GIT; and displaying an adequacy indication for the CE procedure based on the adequacy measure.

16 Claims, 23 Drawing Sheets

(51) Int. Cl.
*A61B 1/273* (2006.01)
*G16H 30/00* (2018.01)

(56) References Cited

U.S. PATENT DOCUMENTS

| | | | | |
|---|---|---|---|---|
| 9,324,145 | B1 * | 4/2016 | Cherevatsky | A61B 1/000094 |
| 11,478,125 | B2 * | 10/2022 | Dolnik | A61B 5/6861 |
| 11,580,446 | B2 * | 2/2023 | Lee | G06V 10/764 |
| 11,615,527 | B2 * | 3/2023 | Najarian | G06T 7/269<br>382/128 |
| 11,918,178 | B2 * | 3/2024 | Freedman | G06T 7/0016 |
| 12,102,441 | B2 * | 10/2024 | Kim | A61B 5/4255 |
| 12,254,673 | B1 * | 3/2025 | Tsadok | G06V 10/762 |
| 2007/0232851 | A1 * | 10/2007 | Fujimori | A61B 1/041<br>600/109 |
| 2009/0028407 | A1 * | 1/2009 | Seibel | A61B 1/0627<br>382/131 |
| 2009/0259102 | A1 * | 10/2009 | Koninckx | A61B 1/00194<br>348/E13.001 |
| 2009/0305331 | A1 * | 12/2009 | Ben-Horin | G01N 33/50<br>435/29 |
| 2010/0130818 | A1 * | 5/2010 | Jung | A61B 1/00036<br>600/109 |
| 2011/0160534 | A1 * | 6/2011 | Lee | A61B 1/000094<br>600/109 |
| 2012/0207369 | A1 * | 8/2012 | Valadez | A61B 6/03<br>382/131 |
| 2012/0219642 | A1 * | 8/2012 | Nizam | A61K 9/08<br>604/514 |
| 2012/0277181 | A1 * | 11/2012 | Pavliv | A61P 1/10<br>514/53 |
| 2013/0172680 | A1 * | 7/2013 | Polyakov | A61B 1/015<br>600/156 |
| 2013/0296314 | A1 * | 11/2013 | Borody | A61P 1/16<br>514/277 |
| 2015/0117729 | A1 * | 4/2015 | Kim | G06T 7/0012<br>382/128 |
| 2018/0055576 | A1 * | 3/2018 | Koyrakh | A61B 5/113 |
| 2018/0263715 | A1 * | 9/2018 | Maeda | A61B 17/00234 |
| 2019/0200844 | A1 * | 7/2019 | Shelton, IV | H04L 63/123 |
| 2019/0298757 | A1 * | 10/2019 | Bar-Shalom | A61K 31/737 |
| 2020/0107699 | A1 * | 4/2020 | Ariyoshi | A61B 1/233 |
| 2020/0160032 | A1 * | 5/2020 | Allen | G16H 50/30 |
| 2020/0170524 | A1 * | 6/2020 | Assaf | G01N 29/4472 |
| 2020/0175340 | A1 | 6/2020 | Lee et al. | |
| 2020/0305972 | A1 * | 10/2020 | Kadamus | A61B 18/1492 |
| 2020/0310471 | A1 * | 10/2020 | Hogg | A61B 5/065 |
| 2020/0329955 | A1 * | 10/2020 | Nadimi | A61B 1/0638 |
| 2020/0397238 | A1 * | 12/2020 | Dray | G06N 20/20 |
| 2021/0280312 | A1 * | 9/2021 | Freedman | G16H 30/40 |
| 2023/0070807 | A1 * | 3/2023 | Bachwich | G06T 7/0002 |
| 2023/0397794 | A1 * | 12/2023 | Baras | A61B 1/041 |
| 2024/0013509 | A1 * | 1/2024 | Cherubini | G06V 20/47 |
| 2024/0249829 | A1 * | 7/2024 | Dekel | G16H 30/40 |
| 2025/0000349 | A1 * | 1/2025 | Dekel | G06T 7/70 |
| 2025/0120582 | A1 * | 4/2025 | Montague | A61B 5/0075 |

FOREIGN PATENT DOCUMENTS

| | | | |
|---|---|---|---|
| WO | 2019175248 | A1 | 9/2019 |
| WO | 2020079667 | A1 | 4/2020 |
| WO | 2020079696 | A1 | 4/2020 |

OTHER PUBLICATIONS

European Examination Report for Application No. 21 786 600.3 dated Jul. 16, 2025, 5 pages.

Japanese Office Action for Application No. 2023-515283 dated Jun. 26, 2025 with English translation, 8 pages.

European Communication for Application No. 21 786 600.3 dated May 29, 2026, 9 pages.

* cited by examiner

ESTIMATING THE ADEQUACY OF A PROCEDURE

CROSS-REFERENCE TO RELATED APPLICATION

The present application is a U.S. National Stage Application filed under 35 U.S.C. § 371(a) of International Patent Application No. PCT/IL2021/051074, filed Sep. 1, 2021, which claims the benefit of and priority to U.S. Provisional Patent Application Ser. No. 63/075,778, filed on Sep. 8, 2020, and U.S. Provisional Patent Application Ser. No. 63/228,937, filed on Aug. 3, 2021. The entire content of each of the foregoing applications are hereby incorporated by reference.

FIELD

The disclosure relates to image analysis methods and systems and, more particularly, to systems and methods for analyzing a stream of images captured via a Capsule Endoscopy procedure to estimate an adequacy of the procedure.

BACKGROUND

Capsule endoscopy (CE) allows examining the entire gastrointestinal tract (GIT) endoscopically. There are capsule endoscopy systems and methods that are aimed at examining a specific portion of the GIT, such as the small bowel (SB) or the colon. CE is a non-invasive procedure that does not require the patient to be admitted to a hospital, and the patient can continue most daily activities while the capsule is in his body.

On a typical CE procedure, the patient is referred to a procedure by a physician. The patient then arrives at a medical facility (e.g., a clinic or a hospital), to perform the procedure. The capsule, which is about the size of a multi-vitamin, is swallowed by the patient under the supervision of a health professional (e.g., a nurse or a physician) at the medical facility and the patient is provided with a wearable device, e.g., a sensor belt and a recorder placed in a pouch and strap to be placed around the patient's shoulder. The wearable device typically includes a storage device. The patient may be given guidance and/or instructions and then released to his daily activities.

The capsule captures images as it travels naturally through the GIT. Images and additional data (e.g., metadata) are then transmitted to the recorder that is worn by the patient. The capsule is typically disposable and passes naturally with a bowel movement. The procedure data (e.g., the captured images or a portion of them and additional metadata) is stored on the storage device of the wearable device.

The wearable device is typically returned by the patient to the medical facility with the procedure data stored thereon. The procedure data is then downloaded to a computing device typically located at the medical facility, which has an engine software stored thereon. The received procedure data is then processed by the engine to a compiled study (or "study"). Typically, a study includes thousands of images (around 8,000-10,000). Typically, the number of images to be processed is of the order of tens of thousands and about 100,000 on average.

A reader (which may be the procedure supervising physician, a dedicated physician, or the referring physician) may access the study via a reader application. The reader then reviews the study, evaluates the procedure, and provides his input via the reader application. Since the reader needs to review thousands of images, the reading time of a study may usually take between half an hour to an hour on average, and the reading task may be tiresome. A report is then generated by the reader application based on the compiled study and the reader's input. On average, it would take an hour to generate a report. The report may include, for example, images of interest, e.g., images which are identified as including pathologies, selected by the reader; evaluation or diagnosis of the patient's medical condition based on the procedure's data (i.e., the study) and/or recommendations for follow up and/or treatment provided by the reader. The report may then be forwarded to the referring physician. The referring physician may decide on a required follow up or treatment based on the report.

SUMMARY

The present disclosure relates to systems and methods for analyzing a stream of images of a gastrointestinal tract (GIT). More particularly, the present disclosure relates to systems and methods for analyzing a stream of images, after a Capsule Endoscopy (CE) procedure is completed, to estimate the adequacy of the CE procedure for capturing an event of interest, e.g., estimating whether the imaging coverage of the stream of images was adequate to visualize at least one polyp (whether or not any actually exist). In various aspects, the at least one polyp may include a significant polyp, such as a polyp of a size of about 6 mm or greater. As described herein, when it is not possible to determine the adequacy of a CE procedure by constructing a three-dimensional view of a GIT or portion of a GIT using images captured in vivo by a CE imaging device, other measures and/or indicators are used to determine the adequacy of a CE procedure. The present disclosure may provide for the exclusion (e.g., either by a clinician and/or automatically) of a CE procedure when imaging coverage of the stream of images is estimated to not be adequate to visualize at least one polyp (whether or not any actually exist) and may, thereby, significantly reduce the percentage of people who have a polyp but are incorrectly cleared by the capsule endoscopy procedure as having no visualized polyp. Where a CE procedure is estimated to be adequate to visualize at least one polyp (whether or not any actually exist), the present disclosure may also provide for more confident exclusion of cases without any polyps.

Even though examples are shown and described with respect to images captured in vivo by a capsule endoscopy device, the disclosed technology can be applied to images captured by other devices or mechanisms. Further, to the extent consistent, any or all of the aspects detailed herein may be used in conjunction with any or all of the other aspects detailed herein.

Provided in accordance with aspects of the disclosure is a computer-implemented method for estimating the adequacy of a capsule endoscopy (CE) procedure, including accessing a plurality of images of at least a portion of a gastrointestinal tract (GIT) captured by a CE device during a CE procedure; determining an adequacy measure for the CE procedure, the adequacy measure indicating a measurement for effectiveness of the CE procedure in capturing a predefined event in the plurality of images; and displaying the adequacy measure on a display.

In an aspect of the present disclosure, the adequacy measure for the procedure may be determined based on pre-defined characteristics of a CE procedure.

In an aspect of the present disclosure, the predefined event may include a type of pathology, at least one occurrence of a type of pathology, all the occurrences of a type of pathology in a predefined portion of the GIT, at least one occurrence of a type of a pathology of a predefined size, all of the occurrences of a type of a pathology of a predefined size in a predefined portion of the GIT, polyps, at least one occurrence of a polyp, all the occurrences of polyps in the colon, at least one occurrence of polyp larger than a predefined size in the colon, all of the occurrences of polyps larger than a predefined size in the colon, a parasite, a disease indicator, and/or a disease appearance.

In another aspect of the present disclosure, the predefined event may a periodic event, a temporary event, and/or a constant event.

In another aspect of the present disclosure, the method may further include providing an indication of whether or not to exclude a study based on the CE procedure from being generated, wherein the determination is based on the determined adequacy measure.

In still another aspect of the present disclosure, the method may further include excluding from generating a study based on the determined adequacy measure.

In yet another aspect of the present disclosure, the method may further include in a case where the CE procedure was excluded: receiving a probability score indicating if the predefined event is included in the accessed images; and generating a study for the previously excluded CE procedure based on the probability score for the event being above a predetermined threshold.

In an aspect of the present disclosure, the adequacy measure may be determined based on a classical machine learning technique, a deep learning technique, and/or a heuristic.

In an aspect of the present disclosure, the characteristic measure may include a segmental characteristic or a global-per procedure characteristic.

In another aspect of the present disclosure, each image of the plurality of images of the GIT may be associated with one segment of the plurality of consecutive segments of the GIT. The method may further include determining the segmental adequacy measure for each segment of the plurality of consecutive segments of the GIT based one or more segmental characteristics.

In another aspect of the present disclosure, the segmental characteristics may be selected from the group consisting of: a motion score, or a score indicative of an average cleansing level per segment.

In still yet another aspect of the present disclosure, the adequacy measure may further be determined based on a segment adequacy probability based on multiplying at least two of a motion score, a cleansing level per segment, and/or a transit time.

In an aspect of the present disclosure, the global-per procedure adequacy measure may be based on an average cleansing score over all of the segments, a demographic of a patient, a last segment of the GIT that the CE device reached, and/or an absolute time the CE device spent in the portion of the GIT.

In another aspect of the present disclosure, the characteristic measure may include an anatomical colon segment associated with the image, a transit pattern of the capsule endoscopy device, CE device communication errors, an anatomical landmark in the plurality of images, and/or coverage of GIT tissue in the plurality of images Provided in accordance with aspects of the disclosure is a system for estimating the adequacy of a capsule endoscopy (CE) procedure. The system includes a display, at least one processor, and at least one memory. The memory includes instructions stored thereon which, when executed by the at least one processor, cause the system to access a plurality of images of at least a portion of a gastrointestinal tract (GIT) captured by a CE device during a CE procedure; determine an adequacy measure for the CE procedure, the adequacy measure indicating a measurement for effectiveness of the CE procedure in capturing a predefined event in the plurality of images; and display the adequacy measure on the display.

In another aspect of the present disclosure, the adequacy measure for the procedure may be determined based on pre-defined characteristics of a CE procedure.

In an aspect of the present disclosure, the instructions, when executed by the at least one processor, may further cause the system to provide an indication of whether or not to exclude a study based on the CE procedure from being generated, wherein the determination is based on the determined adequacy measure. Provided in accordance with aspects of the disclosure is a computer-implemented method for estimating adequacy of a capsule endoscopy (CE) procedure, comprising: accessing a plurality of images of at least a portion of a gastrointestinal tract (GIT) captured by a CE device during a CE procedure; determining an adequacy measure for the procedure, the adequacy measure indicating a measurement for effectiveness of the CE procedure in capturing a predefined event in the plurality of images; and excluding from generating a study based on the CE procedure, the excluding based on the adequacy measure being below a predetermined threshold.

In another aspect of the present disclosure, the method may further include indicating to a user that the CE procedure has been excluded.

In another aspect of the present disclosure, the method may further include receiving event scores and including, in the study, the previously excluded CE procedure based on the received event scores being above a predetermined threshold.

In accordance with aspects of the present disclosure, a computer-implemented method for estimating adequacy of a capsule endoscopy (CE) procedure includes: accessing a plurality of images of at least a portion of a gastrointestinal tract (GIT) captured by a CE imaging device during a CE procedure; accessing a plurality of characteristic measures associated with the plurality of images; determining an adequacy measure for the CE procedure based on the plurality of characteristic measures, where the adequacy measure provides a measure of whether an imaging coverage provided by the plurality of images was adequate to capture an event of interest in the at least the portion of the GIT, whether or not such an event of interest actually exists in the at least the portion of the GIT; and displaying an adequacy indication for the CE procedure based on the adequacy measure.

In various embodiments of the computer-implemented method, the method includes processing the plurality of images to identify a plurality of image groups, where in each image group of the plurality of image groups, each image of the respective image group captures the same tissue region.

In various embodiments of the computer-implemented method, a characteristic measure among the plurality of characteristic measures includes, for each image group of the plurality of image groups, a number of images in the respective image group, and the adequacy measure for the CE procedure is determined based on the number of images in each image group of the plurality of image groups.

In various embodiments of the computer-implemented method, a characteristic measure among the plurality of characteristic measures includes, for each image group of the plurality of image groups, an average cleansing ratio for the respective image group, and the adequacy measure for the CE procedure is determined based on the average cleansing ratio of each image group of the plurality of image groups.

In various embodiments of the computer-implemented method, the method includes determining the average cleansing ratio for each image group by accessing a mapping of cleansing scores to cleansing ratios and for each image group of the plurality of image groups: accessing a cleansing score for each image in the respective image group, determining a cleansing ratio for each image in the respective image group based on the mapping of cleansing scores to cleansing ratios, and determining the average cleansing ratio for the respective image group as an average of the cleansing ratios for the images in the respective image group.

In various embodiments of the computer-implemented method, the at least the portion of the GIT includes a plurality of segments. Determining the adequacy measure for the CE procedure includes determining an adequacy measure for each segment of the plurality of segments and determining the adequacy measure for the CE procedure based on the adequacy measure for each segment of the plurality of segments.

In various embodiments of the computer-implemented method, the method further may include determining that the adequacy measure indicates that the imaging coverage provided by the plurality of images was not adequate to capture an event of interest in the at least the portion of the GIT, whether or not such an event of interest actually exists in the at least the portion of the GIT The adequacy indication for the CE procedure includes at least one reason why the CE procedure was determined to be not adequate.

In various embodiments of the computer-implemented method, determining the adequacy measure for the CE procedure based on the adequacy measure for each segment of the plurality of segments includes: accessing a priori probabilities of occurrences of the event of interest in each segment of the plurality of segments, where the a priori probabilities are empirically determined based on a patient population; and determining the adequacy measure for the CE procedure based on the a priori probabilities and based on the adequacy measure for each segment of the plurality of segments.

In various embodiments of the computer-implemented method, the method includes accessing at least one quality measure associated with the plurality of images, determining the adequacy indication based on a first set of adequacy rules when the at least one quality measure is satisfied, and determining the adequacy measure based on a second set of adequacy rules when any of the at least one quality measure is not satisfied.

In accordance with aspects of the present disclosure a system for estimating adequacy of a capsule endoscopy (CE) procedure includes a display device, at least one processor, and at least one memory including instructions stored thereon. The instructions, when executed by the at least one processor, cause the system to: access a plurality of images of at least a portion of a gastrointestinal tract (GIT) captured by a CE imaging device during a CE procedure; access a plurality of characteristic measures associated with the plurality of images; determine an adequacy measure for the CE procedure based on the plurality of characteristic measures, where the adequacy measure provides a measure of whether an imaging coverage provided by the plurality of images was adequate to capture an event of interest in the at least the portion of the GIT, whether or not such an event of interest actually exists in the at least the portion of the GIT; and display, on the display device, an adequacy indication for the CE procedure based on the adequacy measure.

In various embodiments of the system, the instructions, when executed by the at least one processor, further cause the system to process the plurality of images to identify a plurality of image groups, where in each image group of the plurality of image groups, each image of the respective image group captures the same tissue region.

In various embodiments of the system, a characteristic measure among the plurality of characteristic measures includes, for each image group of the plurality of image groups, a number of images in the respective image group, and the adequacy measure for the CE procedure is determined based on the number of images in each image group of the plurality of image groups.

In various embodiments of the system, a characteristic measure among the plurality of characteristic measures includes, for each image group of the plurality of image groups, an average cleansing ratio for the respective image group, and the adequacy measure for the CE procedure is determined based on the average cleansing ratio of each image group of the plurality of image groups.

In various embodiments of the system, the instructions, when executed by the at least one processor, further cause the system to determine the average cleansing ratio for each image group by: accessing a mapping of cleansing scores to cleansing ratios, and for each image group of the plurality of image groups: accessing a cleansing score for each image in the respective image group, determining a cleansing ratio for each image in the respective image group based on the mapping of cleansing scores to cleansing ratios, and determining the average cleansing ratio for the respective image group as an average of the cleansing ratios for the images in the respective image group.

In various embodiments of the system, the at least the portion of the GIT includes a plurality of segments, and determining the adequacy measure for the CE procedure includes: determining an adequacy measure for each segment of the plurality of segments, and determining the adequacy measure for the CE procedure based on the adequacy measure for each segment of the plurality of segments.

In various embodiments of the system, in determining the adequacy measure for the CE procedure based on the adequacy measure for each segment of the plurality of segments, the instructions, when executed by the at least one processor, causes the system to: access a priori probabilities of occurrences of the event of interest in each segment of the plurality of segments, where the a priori probabilities are empirically determined based on a patient population; and determine the adequacy measure for the CE procedure based on the a priori probabilities and based on the adequacy measure for each segment of the plurality of segments.

In various embodiments of the system, the instructions, when executed by the at least one processor, further cause the system to: access at least one quality measure associated with the plurality of images; determine the adequacy indication based on a first set of adequacy rules when the at least one quality measure is satisfied; and determine the adequacy measure based on a second set of adequacy rules when any of the at least one quality measure is not satisfied.

In various embodiments of the system, the instructions, when executed by the at least one processor, may cause the system to determine that the adequacy measure indicates that the imaging coverage provided by the plurality of images was not adequate to capture an event of interest in the at least the portion of the GIT, whether or not such an event of interest actually exists in the at least the portion of the GIT, and the adequacy indication for the CE procedure includes at least one reason why the CE procedure was determined to be not adequate.

In various embodiments of the system, the event of interest is a significant polyp, and the instructions, when executed by the at least one processor, may cause the system to determine that the adequacy measure indicates that the imaging coverage provided by the plurality of images was not adequate to capture an event of interest in the at least the portion of the GIT, whether or not such an event of interest actually exists in the at least the portion of the GIT, and determine that a significant polyp was detected in the plurality of images by a polyp detector which processed the plurality of images. The adequacy indication for the CE procedure can include an indication that the CE procedure was determined to be not adequate but that the determination was overruled by a polyp detector.

In accordance with aspects of the present disclosure, a non-transitory computer-readable medium stores instructions which, when executed by a processor, cause performance of a method that includes: accessing a plurality of images of at least a portion of a gastrointestinal tract (GIT) captured by a CE imaging device during a CE procedure; accessing a plurality of characteristic measures associated with the plurality of images; determining an adequacy measure for the CE procedure based on the plurality of characteristic measures, where the adequacy measure provides a measure of whether an imaging coverage provided by the plurality of images was adequate to capture an event of interest in the at least the portion of the GIT, whether or not such an event of interest actually exists in the at least the portion of the GIT; and displaying an adequacy indication for the CE procedure based on the adequacy measure.

In various embodiments of the non-transitory computer-readable medium, the instructions, when executed by the processor, cause further performance of the method including: accessing at least one quality measure associated with the plurality of images, determining the adequacy indication based on a first set of adequacy rules when the at least one quality measure is satisfied, and determining the adequacy measure based on a second set of adequacy rules when any of the at least one quality measure is not satisfied.

Further details and aspects of exemplary embodiments of the present disclosure are described in more detail below with reference to the appended figures.

BRIEF DESCRIPTION OF DRAWINGS

The above and other aspects and features of the disclosure will become more apparent in view of the following detailed description when taken in conjunction with the accompanying drawings wherein like reference numerals identify similar or identical elements.

DETAILED DESCRIPTION

Figure 1:
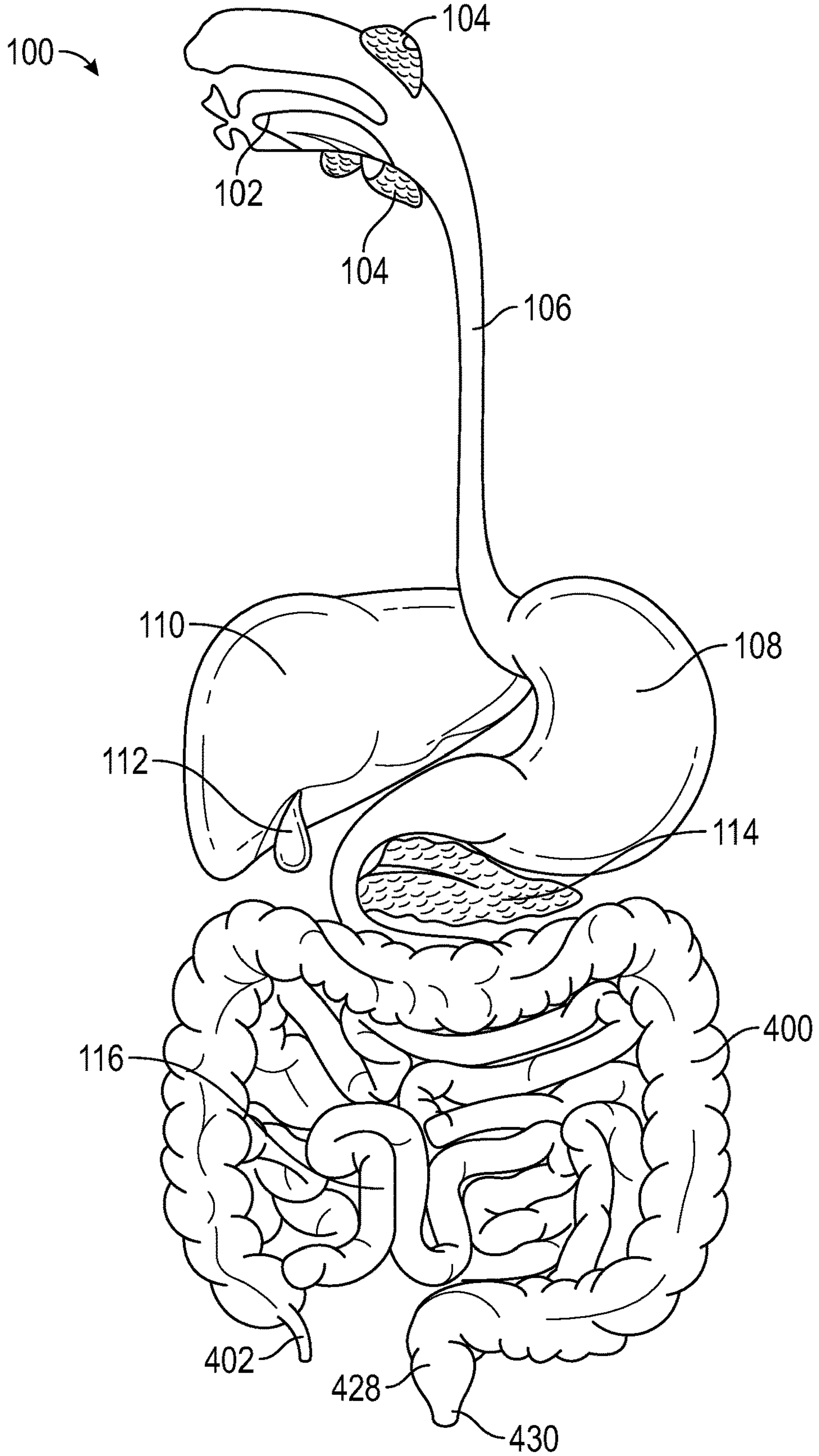
FIG. 1 is a diagram illustrating a gastrointestinal tract (GIT)

The disclosure relates to systems and methods for analyzing medical images and, more particularly, to systems and methods for estimating the adequacy of a capsule endoscopy (CE) procedure after the CE procedure is completed, e.g., estimating whether the imaging coverage provided by a stream of images captured in vivo via a Capsule Endoscopy (CE) procedure was adequate to capture at least one polyp or other event of interest (whether or not any actually exist). The estimated adequacy of the procedure may be used by a clinician to understand whether a CE procedure was adequate to capture an event of interest (whether or not any actually exist). The estimated adequacy of the CE procedure may also be used to automatically exclude a procedure from a study, when the procedure is estimated to be inadequate. Even though examples are shown and described with respect to images captured in vivo by a CE device, the disclosed technology can be applied to images captured by other devices or mechanisms.

The term "adequacy" and its derivatives, as referred to herein with respect to a procedure, may refer to a measure of whether the imaging coverage provided by a stream of images captured by the procedure was adequate to capture an event of interest (whether or not any actually exist).

The term "excluded" and its derivatives, as referred to herein with respect to a procedure, may include providing an indication that the CE procedure was not adequate to capture an event of interest, and/or the CE procedure results are of a quality below a threshold level. For example, the images may be very unclear and/or the results may be missing a lot of images due to connectivity issues between the CE device and the system. According to aspects, a CE study is not generated for an excluded procedure.

The terms "pre-defined event" and "event of interest" and their derivatives, as referred to herein with respect to a procedure, may be and include a periodic event (such as a contraction), a temporary event (such as fresh bleeding), or a constant event (such as a polyp since it has first appeared), among other things. The terms "pre-defined event" and "event of interest" may also include, but are not limited to, for example: a type of pathology, at least one occurrence of a type of pathology, all the occurrences of a type of pathology in a portion of the GIT, at least one occurrence of a type of a pathology of a size, all of the occurrences of a type of a pathology of a size in a portion of the GIT, polyps, at least one occurrence of a polyp, all the occurrences of polyps in the colon, at least one occurrence of polyp larger than a size in the colon, all of the occurrences of polyps larger than a size in the colon, a parasite, disease indicators or appearance, a contraction, fresh bleeding, stricture, and/or a disease, among other things.

The term "characteristic measure" and its derivatives, as referred to herein with respect to a procedure, may be or may include a measure of whether a characteristic is present or absent, or a degree to which such characteristic may be present or absent. In various embodiments, the value of a characteristic measure may be determined by processing a stream of images captured by a CE procedure. It is contemplated that some characteristic measures may be binary (e.g., retention: does it exist or not), and some characteristic measures may be a score (e.g., gastrointestinal cleansing score).

In the following detailed description, specific details are set forth in order to provide a thorough understanding of the disclosure. However, it will be understood by those skilled in the art that the disclosure may be practiced without these specific details. In other instances, well-known methods, procedures, and components have not been described in detail so as not to obscure the present disclosure. Some features or elements described with respect to one system may be combined with features or elements described with respect to other systems. For the sake of clarity, discussion of same or similar features or elements may not be repeated.

Although the disclosure is not limited in this regard, discussions utilizing terms such as, for example, "processing," "computing," "calculating," "determining," "establishing," "analyzing," "checking," or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium that may store instructions to perform operations and/or processes. Although the disclosure is not limited in this regard, the terms "plurality" and "a plurality" as used herein may include, for example, "multiple" or "two or more." The terms "plurality" or "a plurality" may be used throughout the specification to describe two or more components, devices, elements, units, parameters, or the like. The term set, when used herein, may include one or more items. Unless explicitly stated, the methods described herein are not constrained to a particular order or sequence.

Additionally, some of the described methods or elements thereof can occur or be performed simultaneously, at the same point in time, or concurrently. The term "classification" may be used throughout the specification to indicate a decision that assigns one category among a set of categories to an image/frame. The term "classification scores" may be used throughout the specification to describe a vector of values generated by a machine learning system/model for a set of categories applicable to an image/frame. The term "classification probabilities" may be used throughout the specification to describe a transformation of classification scores into values that reflect probabilities that each category of the set of categories applies to the image/frame. The transformation may involve the use of other factors, values or functions and may use one or more algorithms, including machine learning systems/models.

The term "location" and its derivatives, as referred to herein with respect to an image, may refer to the estimated location of the capsule along the GIT while capturing the image or to the estimated location of the portion of the GIT shown in the image along the GIT.

A type of CE procedure may be determined based on, inter alia, the portion of the GIT that is of interest and is to be imaged (e.g., the colon or the small bowel ("SB")), or based on the specific use (e.g., for checking the status of a GI disease, such as Crohn's disease, or for colon cancer screening).

The terms "surrounding" or "adjacent" as referred to herein with respect to images (e.g., images that surround another image(s), or that are adjacent to other image(s)), may relate to spatial and/or temporal characteristics unless specifically indicated otherwise. For example, images that surround or are adjacent to other image(s) may be images that are estimated to be located near the other image(s) along the GIT and/or images that were captured near the capture time of another image, within a certain threshold, e.g., within one or two centimeters, or within one, five, or ten seconds.

The terms "GIT" and "a portion of the GIT" may each refer to or include the other, according to their context. Thus, the term "a portion of the GIT" may also refer to the entire GIT, and the term "GIT" may also refer only to a portion of the GIT. As used herein, the term "segmentation" may refer to the identification of one or more transition points in a stream of images.

As used herein, the terms "segmentation" or "division" may refer to the identification of one or more transition points between segments or portions of a gastrointestinal tract (GIT) in a stream of images.

As used herein, the term "distal" refers to a portion of the GIT that is farther from the mouth of a person, while the term "proximal" refers to a portion of the GIT that is closer to the mouth of the person.

The terms "image" and "frame" may each refer to or include the other and may be used interchangeably in the present disclosure to refer to a single capture by an imaging device. For convenience, the term "image" may be used more frequently in the present disclosure, but it will be understood that references to an image shall apply to a frame as well.

The term "classification score(s)" or "score(s)" may be used throughout the specification to indicate a value or a vector of values for a category or a set of categories applicable to an image/frame. In various implementations, the value or vector of values of a classification score or classification scores may be or may reflect probabilities. In various embodiments, a model may output classification scores which may be probabilities. In various embodiments, a model may output classification scores which may not be probabilities.

The term "classification probabilities" may be used to describe classification scores which are probabilities or to describe a transformation of classification scores which are not probabilities into values which reflect the probabilities that each category of the set of categories applies to the image/frame. It will be understood from context that various references to "probability" refer to and are a shorthand for a classification probability.

As used herein, a "machine learning system" means and includes any computing system that implements any type of machine learning. As used herein, "deep learning neural network" refers to and includes a neural network having several hidden layers and which does not require feature selection or feature engineering. A "classical" machine learning system, in contrast, is a machine learning system which requires feature selection or feature engineering.

Referring to FIG. 1, an illustration of the GIT 100 is shown. The GIT 100 is an organ system within humans and other animals. The GIT 100 generally includes a mouth 102 for taking in sustenance, salivary glands 104 for producing saliva, an esophagus 106 through which food passes aided by contractions, a stomach 108 to secret enzymes and stomach acid to aid in digesting food, a liver 110, a gall bladder 112, a pancreas 114, a small intestine 116 (e.g., SB) for the absorption of nutrients, and a colon 400 (e.g., large intestine) for storing water and waste material as feces prior to defecation. The colon 400 generally includes an appendix 402, a rectum 428, and an anus 430. Food taken in through the mouth is digested by the GIT to take in nutrients, and the remaining waste is expelled as feces through the anus 430.

Studies of different portions of the GIT 100 (e.g., SB), colon 400, esophagus 106, and/or stomach 108 may be presented via a suitable user interface. As used herein, the term "study" refers to and includes at least a set of images selected from the images captured by a CE imaging device (e.g., 212, FIG. 2) during a single CE procedure performed with respect to a specific patient and at a specific time, and can optionally include information other than images as well. The type of procedure performed may determine which portion of the GIT 100 is the portion of interest. Examples of types of procedures performed include, without limitation, an SB procedure, a colon procedure, an SB and colon procedure, a procedure aimed to specifically exhibit or check the SB, a procedure aimed to specifically exhibit or check the colon, a procedure aimed to specifically exhibit or check the colon and the SB, or a procedure to exhibit or check the entire GIT: esophagus, stomach, SB and colon.

Figure 2:
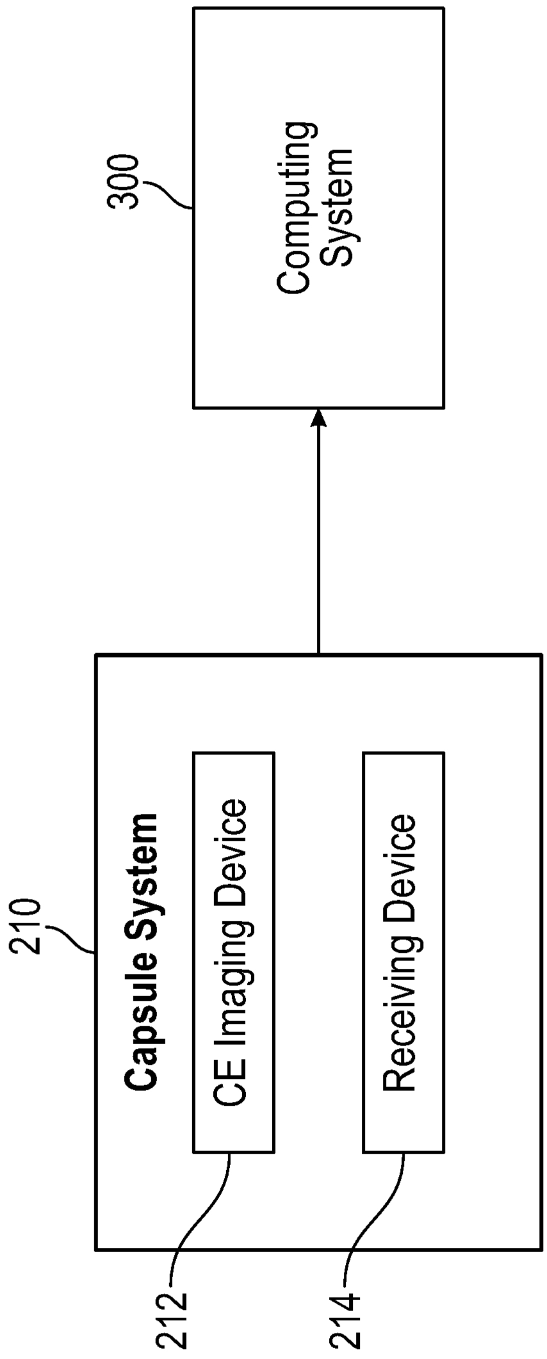
FIG. 2 is a block diagram of an exemplary system for analyzing medical images captured in vivo via a Capsule Endoscopy (CE) procedure in accordance with aspects of the disclosure.

FIG. 2 shows a block diagram of a system for analyzing medical images captured in vivo via a CE procedure. The system generally includes a capsule system 210 configured to capture images of the GIT, and a computing system 300 (e.g., local system and/or cloud system) configured to process the captured images.

The capsule system 210 may include a swallowable CE imaging device 212 (e.g., a capsule) configured to capture images of the GIT as the CE imaging device 212 travels through the GIT. The images may be stored on the CE imaging device 212 and/or transmitted to a receiving device 214, typically including an antenna. In some capsule systems 210, the receiving device 214 may be located on the patient who swallowed the CE imaging device 212 and may, for example, take the form of a belt worn by the patient or a patch secured to the patient.

The capsule system 210 may be communicatively coupled with the computing system 300 and can communicate captured images to the computing system 300. The computing system 300 may process the received images using image processing technologies, machine learning technologies, and/or signal processing technologies, among other technologies. The computing system 300 can include local computing devices that are local to the patient and/or the patient's treatment facility, a cloud computing platform that is provided by cloud services, or a combination of local computing devices and a cloud computing platform.

In the case where the computing system 300 includes a cloud computing platform, the images captured by the capsule system 210 may be transmitted online to the cloud computing platform. In various embodiments, the images can be transmitted via the receiving device 214 worn or carried by the patient. In various embodiments, the images can be transmitted via the patient's smartphone or via any other device connected to the Internet and which may be coupled with the CE imaging device 212 or the receiving device 214.

Figure 3:
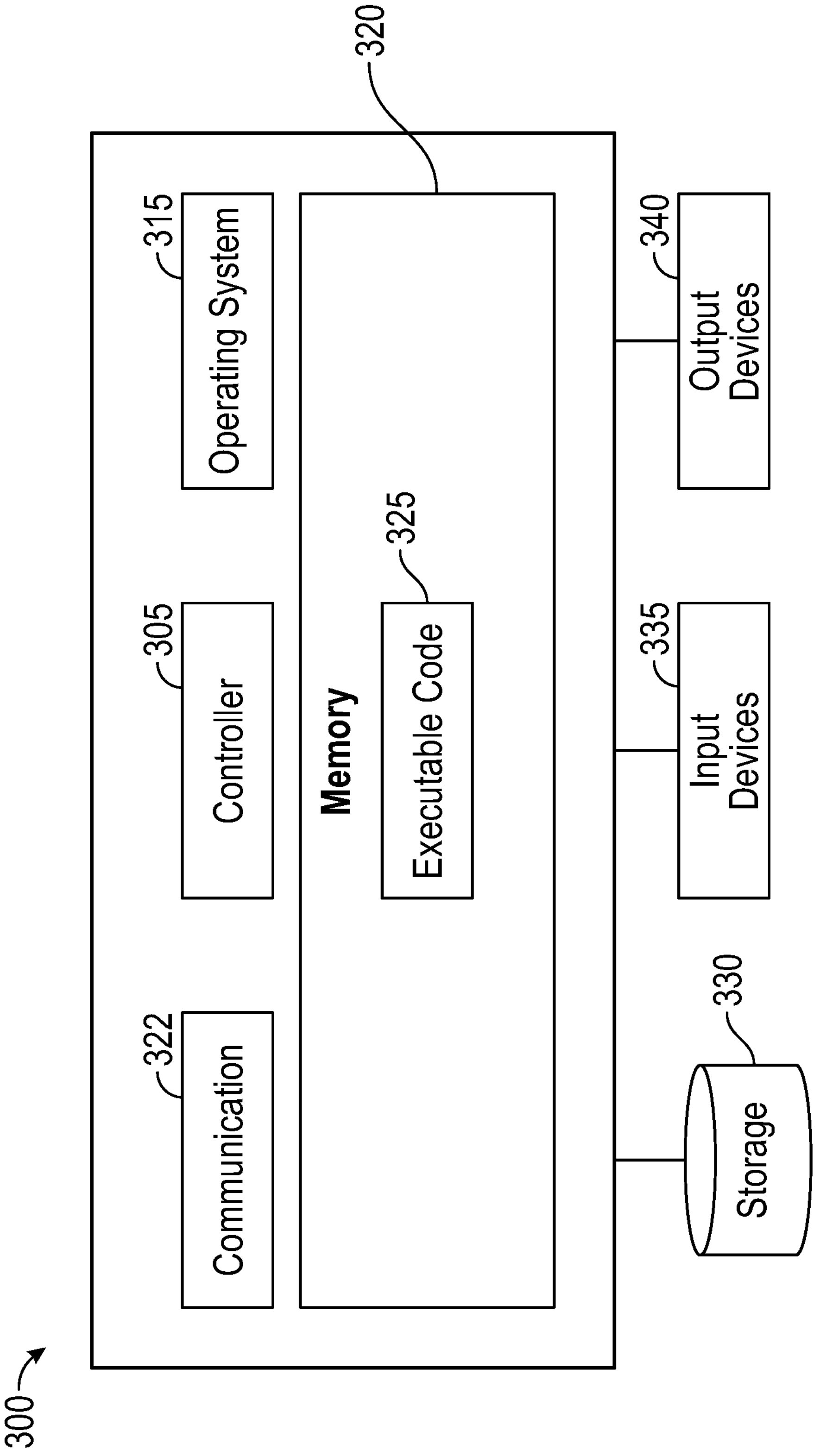
FIG. 3 is a block diagram of an exemplary computing device which may be used with the systems of the disclosure.

FIG. 3 shows a high-level block diagram of an exemplary computing system 300 that may be used with image analyzing systems of the present disclosure. Computing system 300 may include a processor or controller 305 that may be or include, for example, one or more central processing unit processor(s) (CPU), one or more Graphics Processing Unit(s) (GPU or GPGPU), a chip or any suitable computing or computational device, an operating system 215, a memory 320, a storage 330, input devices 335 and output devices 340. Modules or equipment for collecting or receiving (e.g., a receiver worn on a patient) or displaying or selecting for display (e.g., a workstation) medical images collected by the CE imaging device 212 (FIG. 2) may be or include, or may be executed by, the computing system 300 shown in FIG. 3. A communication component 322 of the computing system 300 may allow communications with remote or external devices, e.g., via the Internet or another network, via radio, or via a suitable network protocol such as File Transfer Protocol (FTP), etc.

The computing system 300 includes an operating system 315 that may be or may include any code segment designed and/or configured to perform tasks involving coordination, scheduling, arbitration, supervising, controlling, or otherwise managing operation of computing system 300, for example, scheduling execution of programs. Memory 320 may be or may include, for example, a Random Access Memory (RAM), a read-only memory (ROM), a Dynamic RAM (DRAM), a Synchronous DRAM (SD-RAM), a double data rate (DDR) memory chip, a Flash memory, a volatile memory, a non-volatile memory, a cache memory, a buffer, a short term memory unit, a long term memory unit, or other suitable memory units or storage units. Memory 320 may be or may include a plurality of possibly different memory units. Memory 320 may store, for example, instructions to carry out a method (e.g., executable code 325), and/or data such as user responses, interruptions, etc.

Executable code 325 may be any executable code, e.g., an application, a program, a process, task, or script. Executable code 325 may be executed by controller 305, possibly under the control of operating system 315. For example, execution of executable code 325 may cause the display or selection for display of medical images as described herein. In some systems, more than one computing system 300 or components of computing system 300 may be used for multiple functions described herein. For the various modules and functions described herein, one or more computing systems 300 or components of computing system 300 may be used. Devices that include components similar or different to those included in the computing system 300 may be used and may be connected to a network and used as a system. One or more processor(s) 305 may be configured to carry out methods of the present disclosure by, for example, executing software or code. Storage 330 may be or may include, for example, a hard disk drive, a floppy disk drive, a Compact Disk (CD) drive, a CD-Recordable (CD-R) drive, a universal serial bus (USB) device, or other suitable removable and/or fixed storage unit. Data such as instructions, code, medical images, image streams, etc., may be stored in storage 330 and may be loaded from storage 330 into memory 320 where it may be processed by controller 305. In some embodiments, some of the components shown in FIG. 3 may be omitted.

Input devices 335 may include, for example, a mouse, a keyboard, a touch screen or pad, or any suitable input device. It will be recognized that any suitable number of input devices may be operatively coupled to computing system 300. Output devices 340 may include one or more monitors, screens, displays, speakers, and/or any other suitable output devices. It will be recognized that any suitable number of output devices may be operatively coupled to computing system 300 as shown by block 340. Any applicable input/output (I/O) devices may be operatively coupled to computing system 300, for example, a wired or wireless network interface card (NIC), a modem, printer or facsimile machine, a universal serial bus (USB) device or external hard drive may be included in input devices 335 and/or output devices 340.

Multiple computer systems 300 including some or all of the components shown in FIG. 3 may be used with the described systems and methods. For example, a CE imaging device 212, a receiver, a cloud-based system, and/or a workstation or portable computing device for displaying images may include some or all of the components of the computer system of FIG. 3. A cloud platform (e.g., a remote server) including components such as computing system 300 of FIG. 3 may receive procedure data such as images and metadata, processes and generate a study, and may also display the generated study for the doctor's review (e.g., on a web browser executed on a workstation or portable computer). An "on-premises" option may use a workstation or local server of a medical facility to store, process and display images and/or a study.

Figure 4:
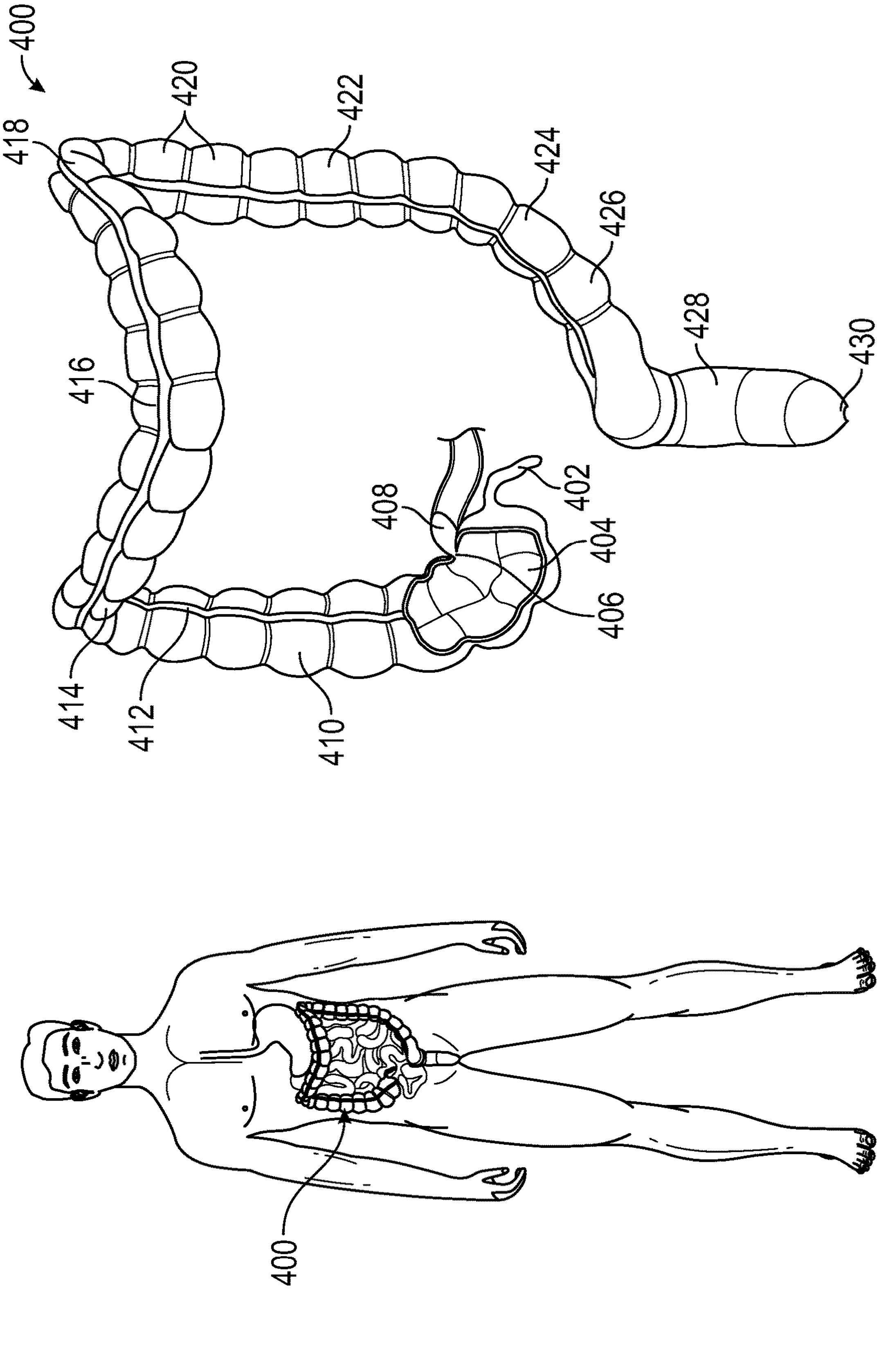
FIG. 4 is a diagram illustrating a large intestine.

According to some aspects of the present disclosure, a user (e.g., a clinician), may build his or her understanding of a case by reviewing a study, which includes a display of images (e.g., captured by the CE imaging device 212) that were selected, e.g., automatically, as images that may be of interest. With reference to FIG. 4, an illustration of the colon 400 is shown. The colon 400 absorbs water, and any remaining waste material is stored as feces before being removed by defecation. The colon 400 may be divided, for example, into five anatomical segments: cecum 404, right or ascending colon 410, transverse colon 416, left or descending colon 422 (e.g., left colon-sigmoid 424), and rectum 428.

A terminal ileum 408 is the final section of the SB and leads to the cecum 404 and is separated from the cecum 404 by a muscle valve called the ileocecal valve (ICV) 406. The ICV 406 also connects the terminal ilium 408 to the ascending colon 410. The cecum 404 is the first section of the colon 400. The cecum 404 includes the appendix 402. The next portion of the colon 400 is the ascending colon 410. The ascending colon 410 is connected to the small bowel by the cecum 404. The ascending colon 410 runs upwards through the abdominal cavity toward the transverse colon 416.

The transverse colon 416 is the part of the colon 400 from the hepatic flexure, also known as the right colic flexure 414 (the turn of the colon 400 by the liver), to the splenic flexure, also known as the left colic flexure 418, (the turn of the colon 400 by the spleen). The transverse colon 416 hangs off the stomach, attached to it by a large fold of peritoneum called the greater omentum. On the posterior side, the transverse colon 416 is connected to the posterior abdominal wall by a mesentery known as the transverse mesocolon.

The descending colon 422 is the part of the colon 400 from the left colic flexure 418 to the beginning of the sigmoid colon 426. One function of the descending colon 422 in the digestive system is to store feces that will be emptied into the rectum. The descending colon 422 is also called the distal gut, as it is further along the gastrointestinal tract than the proximal gut. Gut flora is generally very dense in this region. The sigmoid colon 426 is the part of the colon 400 after the descending colon 422 and before the rectum 428. The name sigmoid means S-shaped. The walls of the sigmoid colon 426 are muscular and contract to increase the pressure inside the colon 400, causing the stool to move into the rectum 428. The sigmoid colon 426 is supplied with blood from several branches (usually between 2 and 6) of the sigmoid arteries.

The rectum 428 is the last section of the colon 400. The rectum 428 holds the formed feces awaiting elimination via defecation.

The CE imaging device 212 (FIG. 2) may be used to image the interior of the colon 400. The entrance from the SB into the colon 400 happens through the ICV 406. Usually, after entering the colon 400 through the ICV 406, the CE imaging device 212 goes into the cecum 404. However, occasionally, the CE imaging device 212 misses the cecum 404 and goes straight into the ascending colon 410. The colon 400 may be wide enough to enable almost unrestricted CE imaging device 212 movement. The CE imaging device 212 may rotate and roll. The CE imaging device 212 may rest in one place for a long period of time, it may move very fast through the colon 400, or it may move back through a prior segment of the colon 400.

In general, the division of the GIT into anatomical segments may be performed, for example, based on the identification of the CE imaging device 212 passage between the different anatomical segments. Such identification may be performed, for example, based on machine learning techniques. It is contemplated that segmentation may also be according to, e.g., sick and healthy segments of the portion of interest, and/or according to specific pathologies, and/or combinations. For example, diseases such as Crohn's are characterized by diffused pathologies that spread on portions of the GIT in an almost "carpet" like manner.

Figure 5:
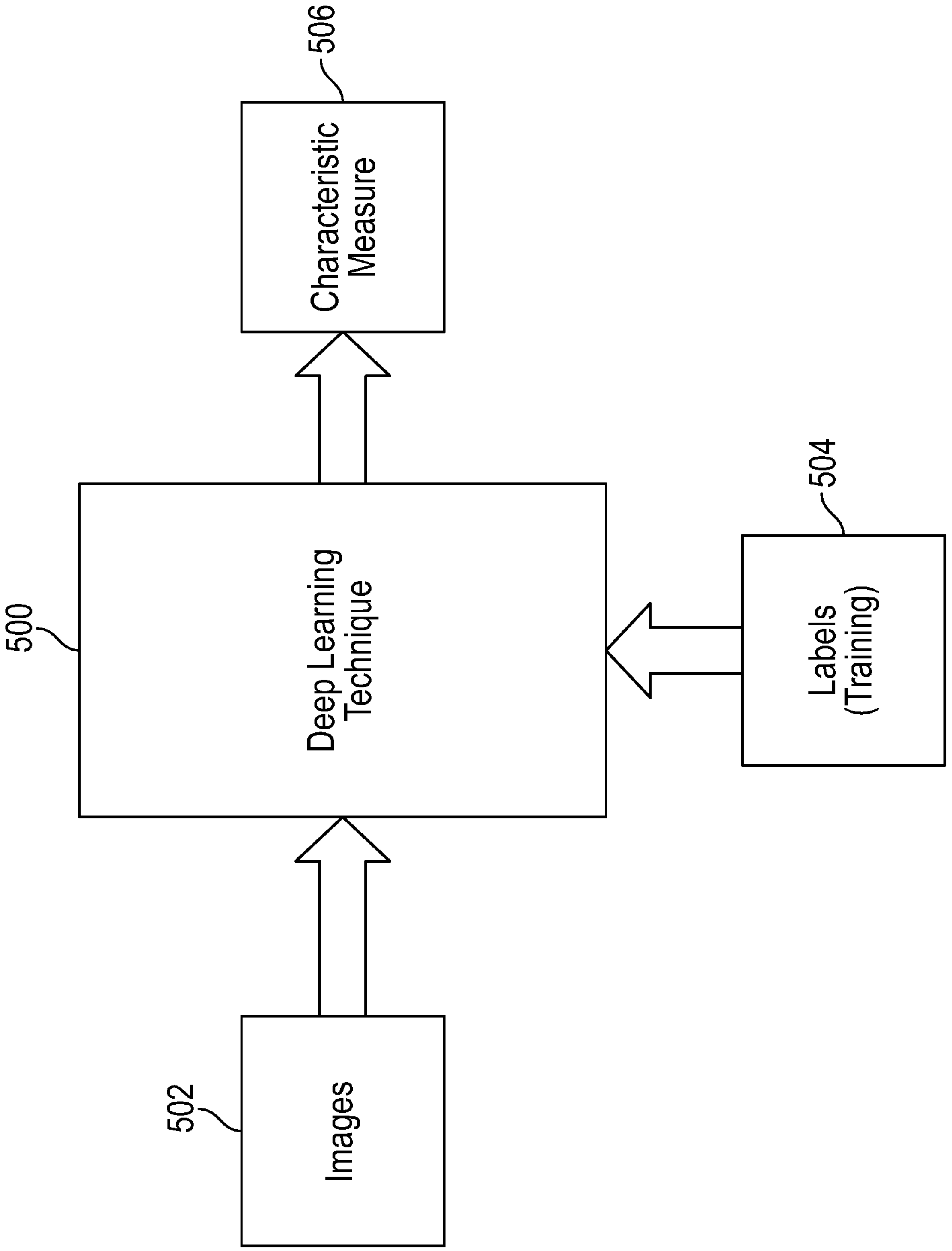
FIG. 5 is a block diagram of an exemplary deep learning neural network and inputs and outputs of a deep learning neural network, in accordance with aspects of the disclosure.

With reference to FIGS. 5, a block diagram for a deep learning neural network 500 for classifying images in accordance with some aspects of the disclosure is shown. In some systems, a deep learning neural network 500 may include a convolutional neural network (CNN) and/or a recurrent neural network. Generally, a deep learning neural network includes multiple hidden layers. As explained in more detail below, the deep learning neural network 500 may leverage one or more CNNs to classify one or more images, taken by the CE imaging device 212 (see FIG. 2), as a portion of the GIT. The deep learning neural network 500 may be executed on the computer system 300 (FIG. 3). Persons skilled in the art will understand the deep learning neural network 500 and how to implement it.

In machine learning, a CNN is a class of artificial neural network (ANN), most commonly applied to analyzing visual imagery. The convolutional aspect of a CNN relates to applying matrix processing operations to localized portions of an image, and the results of those operations (which can involve dozens of different parallel and serial calculations) are sets of many features that are delivered to the next layer. A CNN typically includes convolution layers, activation function layers, deconvolution layers (e.g., in segmentation networks), and/or pooling (typically max pooling) layers to reduce dimensionality without losing too many features. Additional information may be included in the operations that generate these features. Providing unique information that yields features that give the neural networks information can be used to ultimately provide an aggregate way to differentiate between different data input to the neural networks.

Figure 6:
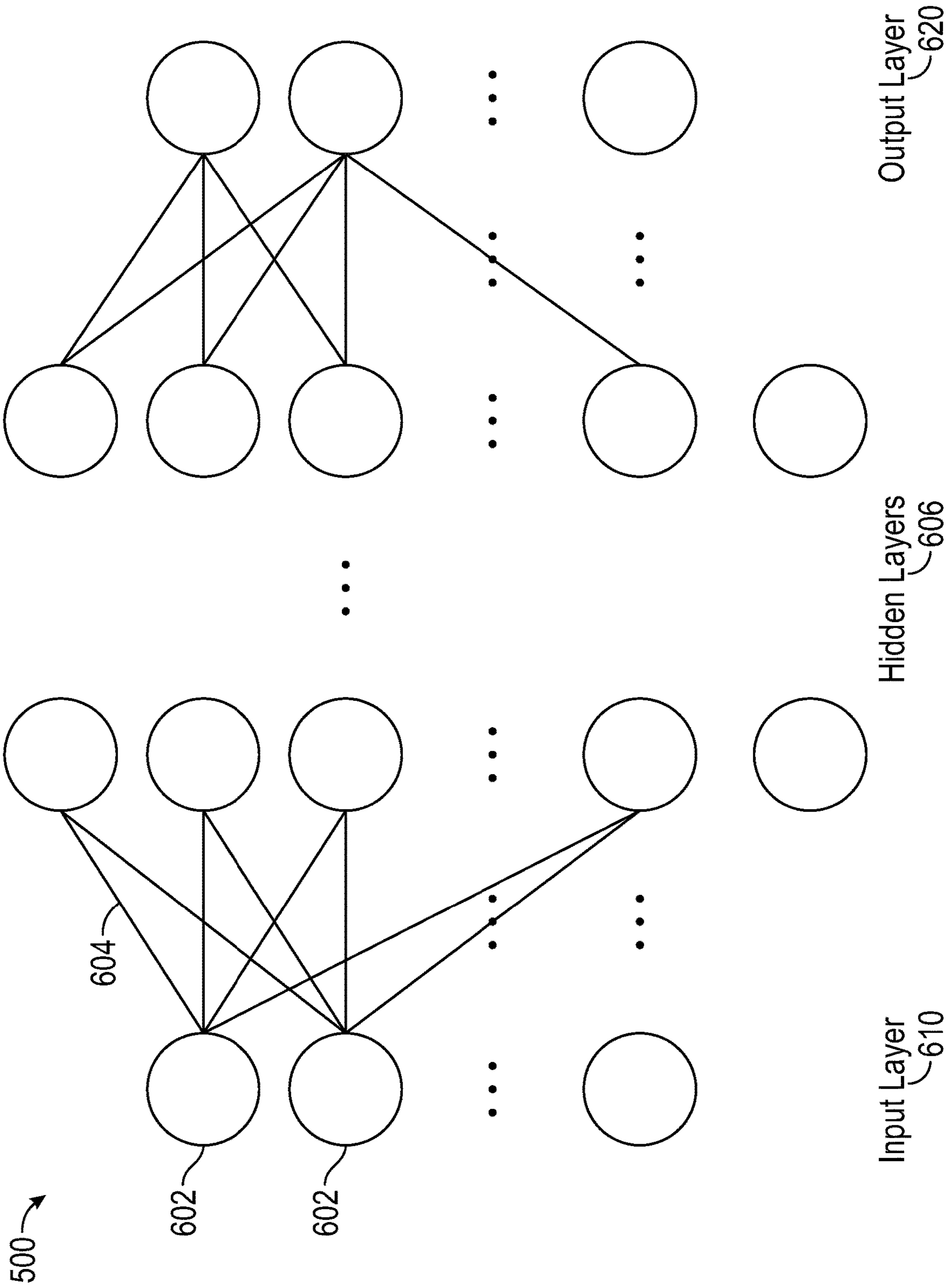
FIG. 6 is a diagram of layers of the deep learning neural network of FIG. 5 in accordance with aspects of the disclosure.

FIG. 6 shows a topology of a deep learning neural network 500, which includes at least one input layer 610, a plurality of hidden layers 606, and at least one output layer 620. The input layer 610, the plurality of hidden layers 606, and the output layer 620 all include neurons 602 (e.g., nodes). The neurons 602 between the various layers are interconnected via weights 604. Each neuron 602 in the deep learning neural network 500 computes an output value by applying a specific function to the input values coming from the previous layer. The function that is applied to the input values is determined by a vector of weights 604 and a bias. Learning, in the deep learning neural network, progresses by making iterative adjustments to these biases and weights. The deep learning neural network 500 may output logits.

Referring again to FIG. 5, the deep learning neural network 500 may be trained based on labeling training images and/or objects in training images. For example, an image may be a portion of the GIT (for example, the rectum or the cecum). In some methods in accordance with this disclosure, the training may include supervised learning. The training further may include augmenting the training images to include adding noise, changing colors, hiding portions of the training images, scaling of the training images, rotating the training images, and/or stretching the training images. Persons skilled in the art will understand training the deep learning neural network 500 and how to implement it.

In some methods in accordance with this disclosure, the deep learning neural network 500 may be used to classify images 502 captured by the CE imaging device 212 (see FIG. 2). The classification of the images 502 may be used to determine classification scores for various characteristic measures 506 for use in determining an adequacy measure for a CE procedure. For example, the image classifications may include classifying an image as an image of the cecum, the ascending colon, the transverse colon, the descending colon, or the rectum. Each of the images may include a classification score for each of the consecutive segments of the GIT. A classification score includes the outputs (e.g., logits) of the classical machine learning classifier 700 after applying a function such as a SoftMax to make the outputs represent probabilities. A characteristic measure, as mentioned above, is a measure of whether the characteristic is present or not in the plurality of images and/or a degree to which the characteristic is present or absent.

Figure 7:
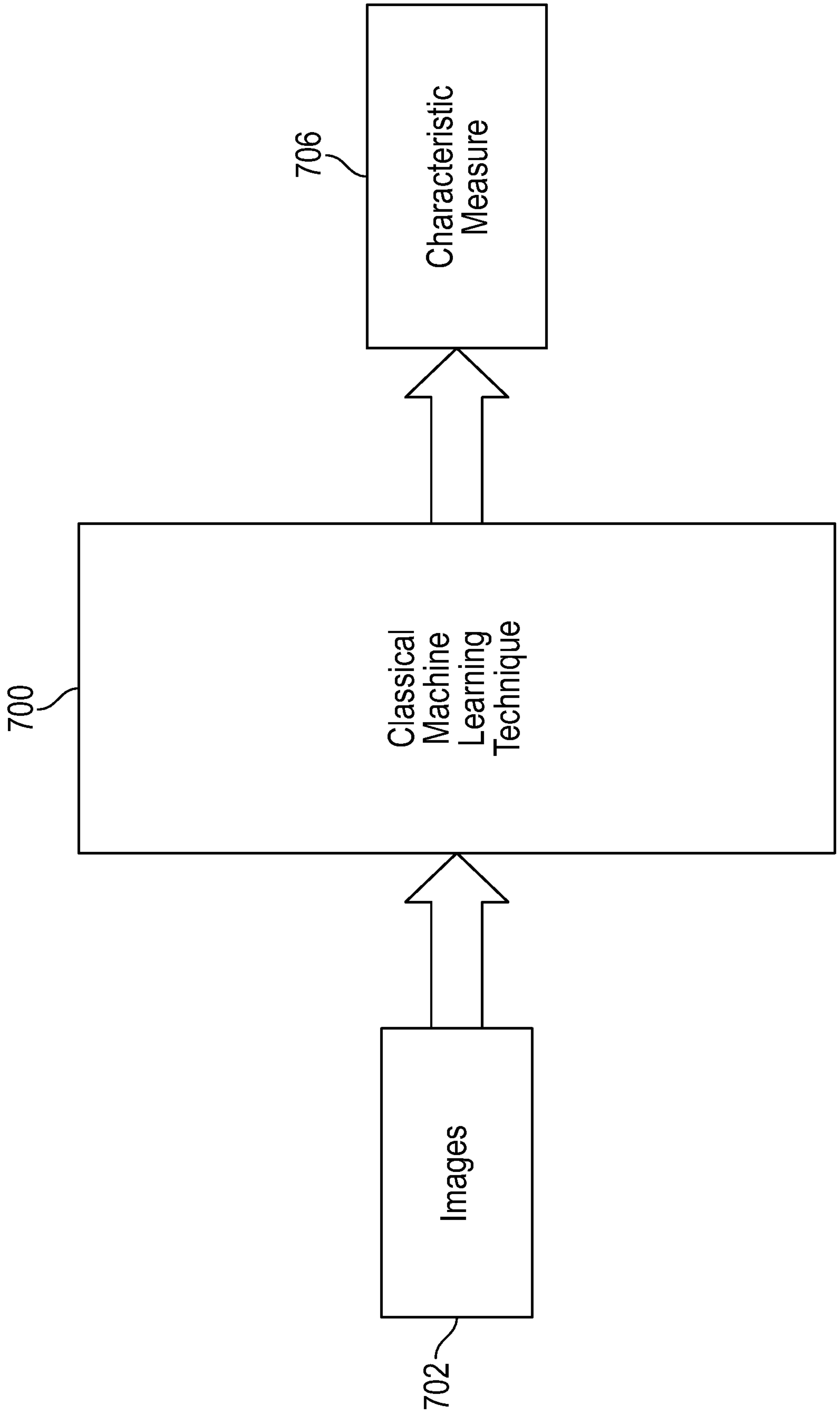
FIG. 7 is a block diagram of an exemplary classical machine learning classifier in accordance with aspects of the disclosure.

With reference to FIG. 7, a classical machine learning classifier 700 is shown in accordance with some aspects of the disclosure. As used herein, the term "classical machine learning classifier" refers to a machine-learning based classifier that requires feature selection and/or feature engineering for inputs to the classifier. In contrast, a deep learning neural network is an example of a machine-learning based classifier that does not require feature engineering or feature selection. As explained in more detail below, the classical machine learning classifier 700 may be configured to provide a score for various characteristic measures, such as a motion score and/or cleansing score. The classical machine learning classifier 700 may include a linear logistic regression classifier, a decision tree, and/or a support vector machine (SVM). In various embodiments, the classical machine learning classifier 700 does not include a CNN or other deep learning network. Persons skilled in the art will understand how to implement such classical machine learning systems.

The linear logistic regression classifier is a classical machine learning classifier. The linear logistic regression classifier estimates the parameters of a logistic model, which best describes the probabilities of each sample to belong to each one of the classes. The linear logistic regression classifier is a supervised learning model. Logistic regression estimates the parameters of a logistic model. The support vector machine is a supervised learning model with associated learning algorithms that analyze data used for classification. In various embodiments, the output of the support vector machine may be normalized between "0" and "1."

In aspects, a SoftMax may be configured to map the non-normalized output of a network (e.g., the logits of the deep learning neural network and/or the classical machine learning classifier 700) to a probability distribution over predicted output classes of one or more of the classification scores (e.g., the classification score of the deep learning neural network). A SoftMax is a function that takes as input a vector of N real numbers and normalizes it into a probability distribution consisting of N probabilities proportional to the exponentials of the input numbers. That is, prior to applying SoftMax, some vector components could be negative, or greater than one, and might not sum to 1. However, after applying SoftMax, each component will be in the interval (0,1), and the components will add up to 1 so that they can be interpreted as probabilities.

The classical machine learning classifier 700 may be trained in a supervised fashion. Images of portions of the GIT may be labeled and used as training data. Persons skilled in the art will understand training the classical machine learning classifier 700 and how to implement it.

In some methods in accordance with this disclosure, the classical machine learning classifier 700 may be used to provide, for images captured by the CE imaging device 212 (see FIG. 2), a classification probability for each segment of the GIT. The classification probability for the images may include each image having a classification probability for a consecutive segment of the GIT. A segment of the GIT may include, but is not limited to, for example, the SB or a portion of it (e.g., where the SB may be divided according to length), or the colon or a portion of it, where, for example, the colon may be divided into segments or regions such as cecum, ascending colon, transverse colon, descending colon, and/or rectum. For example, the image classification probabilities may be labeled as a portion of the colon (e.g., cecum, ascending colon, transverse colon, descending colon, and/or rectum).

Various characteristic measures are described below in connection with FIGS. 8 and 9A-E. Such characteristic measures may be provided by a deep learning neural network (e.g., 500, FIG. 5) and/or by a classical machine learning system (e.g., 700, FIG. 7) or by other techniques. As explained in more detail later herein, the characteristic measures may be used to estimate whether a CE procedure was adequate to capture an event of interest (whether or not any exist). The characteristic measures disclosed below are exemplary, and other characteristic features are contemplated to be within the scope of the present disclosure.

Figure 8:
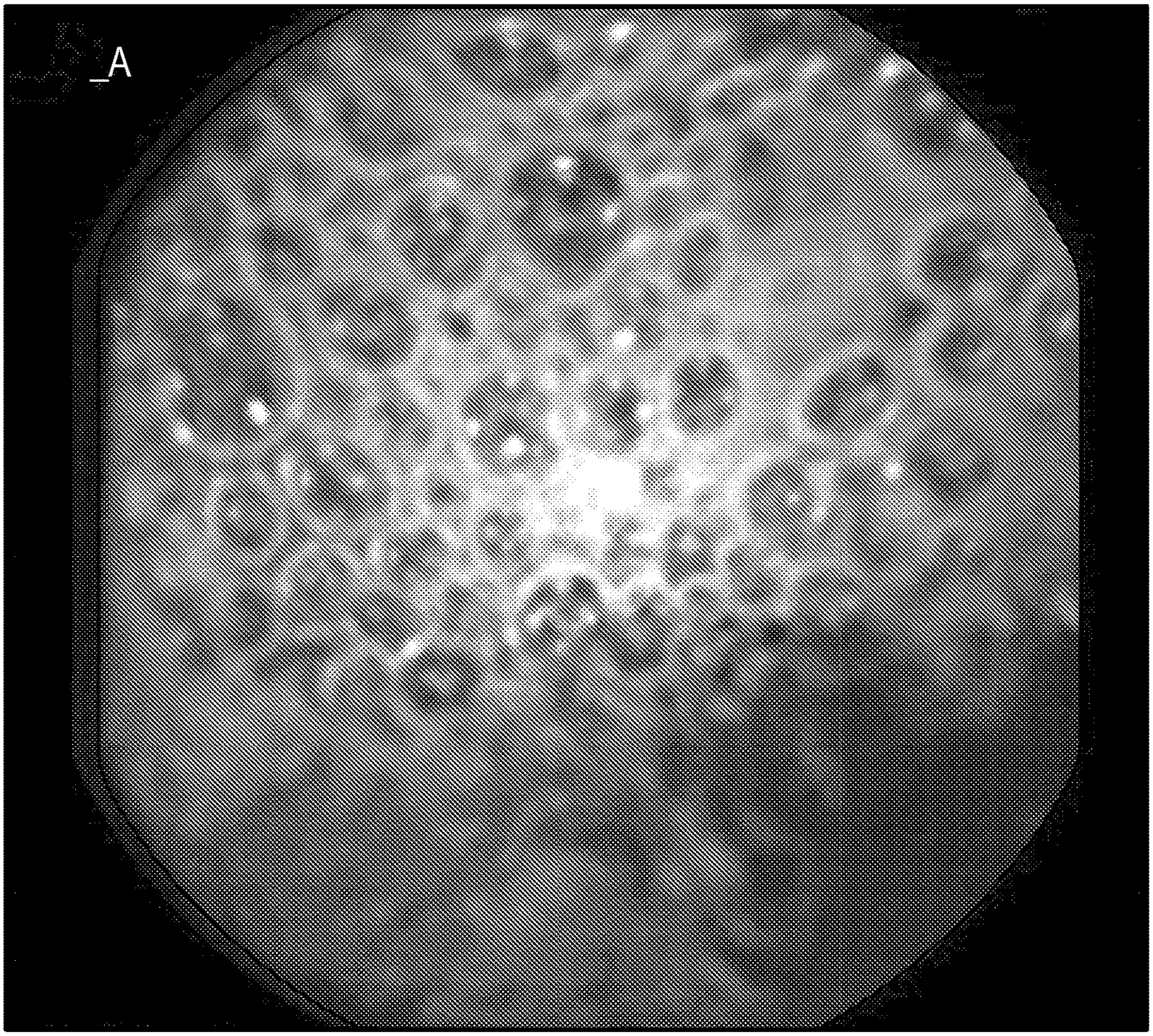
FIG. 8 is an exemplary image captured by the CE device according to FIG. 2 that would have a poor cleansing score in accordance with aspects of the disclosure.

In accordance with aspects of the present disclosure, a characteristic measure may include a cleansing score which indicates a degree of cleansing shown in an image. As persons skilled in the art will understanding, "cleansing" refers to the removal of obstructions from a gastrointestinal tract (GIT) so that the GIT may be effectively imaged. The obstructions may include, for example, fecal matter or bubbles, among other things. FIG. 8 illustrates an exemplary image captured by a CE device that has poor cleansing. The image includes a large amount of fecal residue, which obstructs a clear view of the GIT. In accordance with aspects of the present disclosure, a deep learning neural network (e.g., 500, FIG. 5) and/or a classical machine learning system (e.g., 700, FIG. 7), or another technique, may be used to determine a degree of cleansing for each image of a stream of images captured by a CE procedure. Persons skilled in the art will recognize various ways of determining a cleansing score, such as, for example, using techniques described in: Klein A, Gizbar M, Bourke M, Ahlenstiel G. "A Validated Computerized Cleansing Score for Video Capsule Endoscopy." Dig. Endosc. 2015; 28:564-569, which is hereby incorporated by reference herein in its entirety. Such techniques, and other techniques, for determining a cleansing score are contemplated to be within the scope of the present disclosure.

Figure 9A:
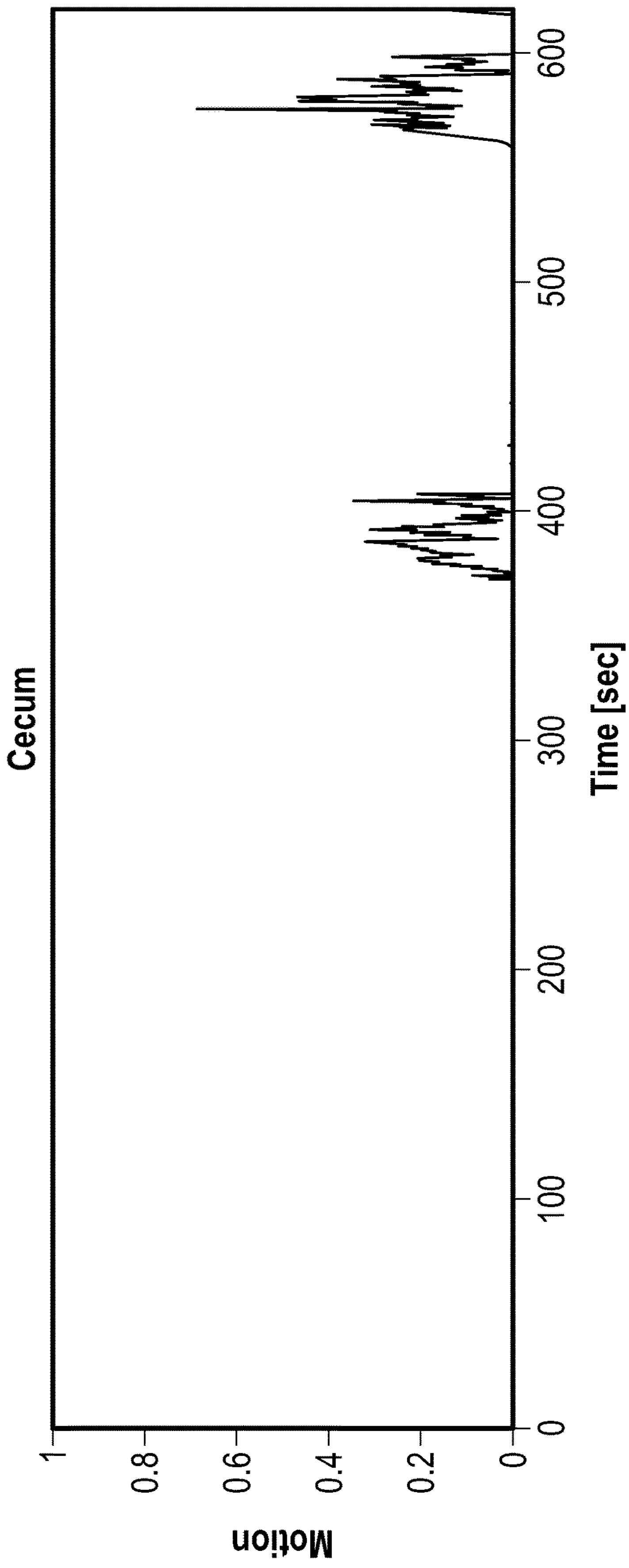
FIG. 9A is an exemplary graph of the output of a motion detector for images of a cecum, in accordance with aspects of the disclosure.
Figure 9B:
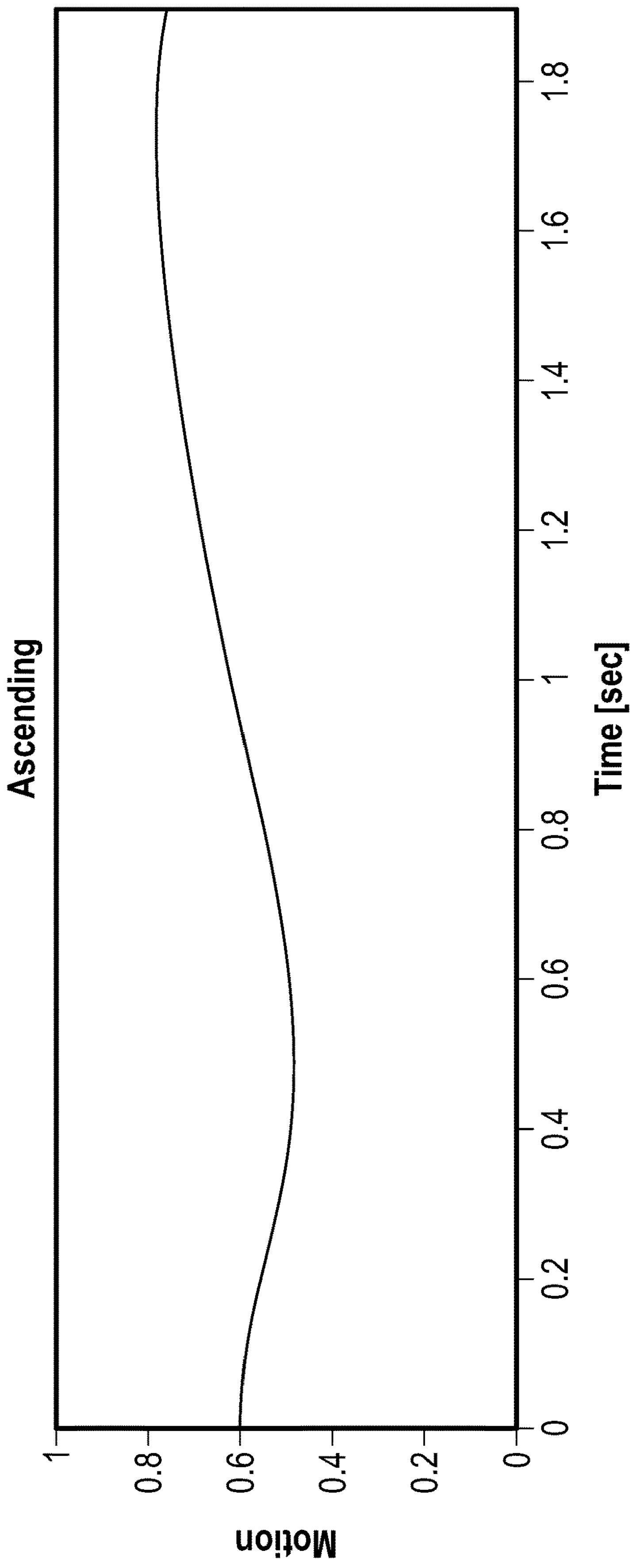
FIG. 9B is an exemplary graph of the output of the motion detector for images of an ascending colon, in accordance with aspects of the disclosure.
Figure 9C:
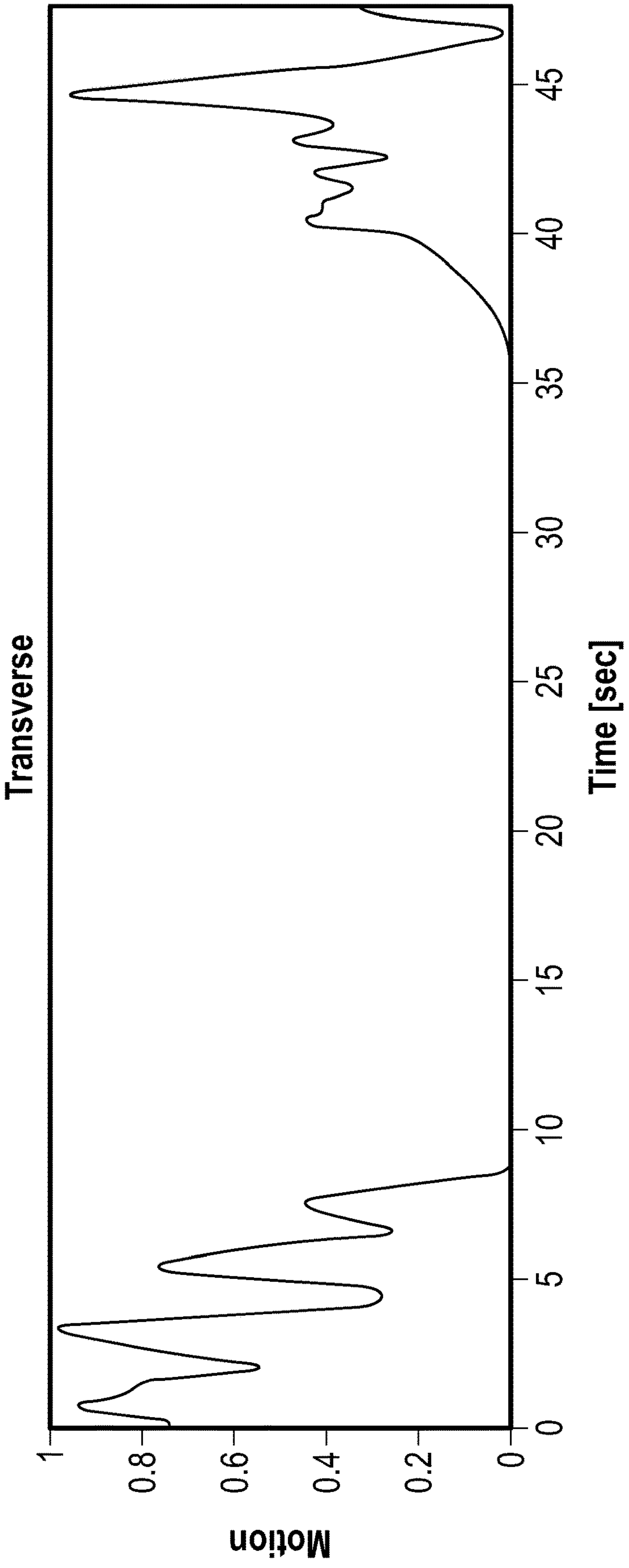
FIG. 9C is an exemplary graph of the output of the motion detector for images of a transverse colon, in accordance with aspects of the disclosure.
Figure 9D:
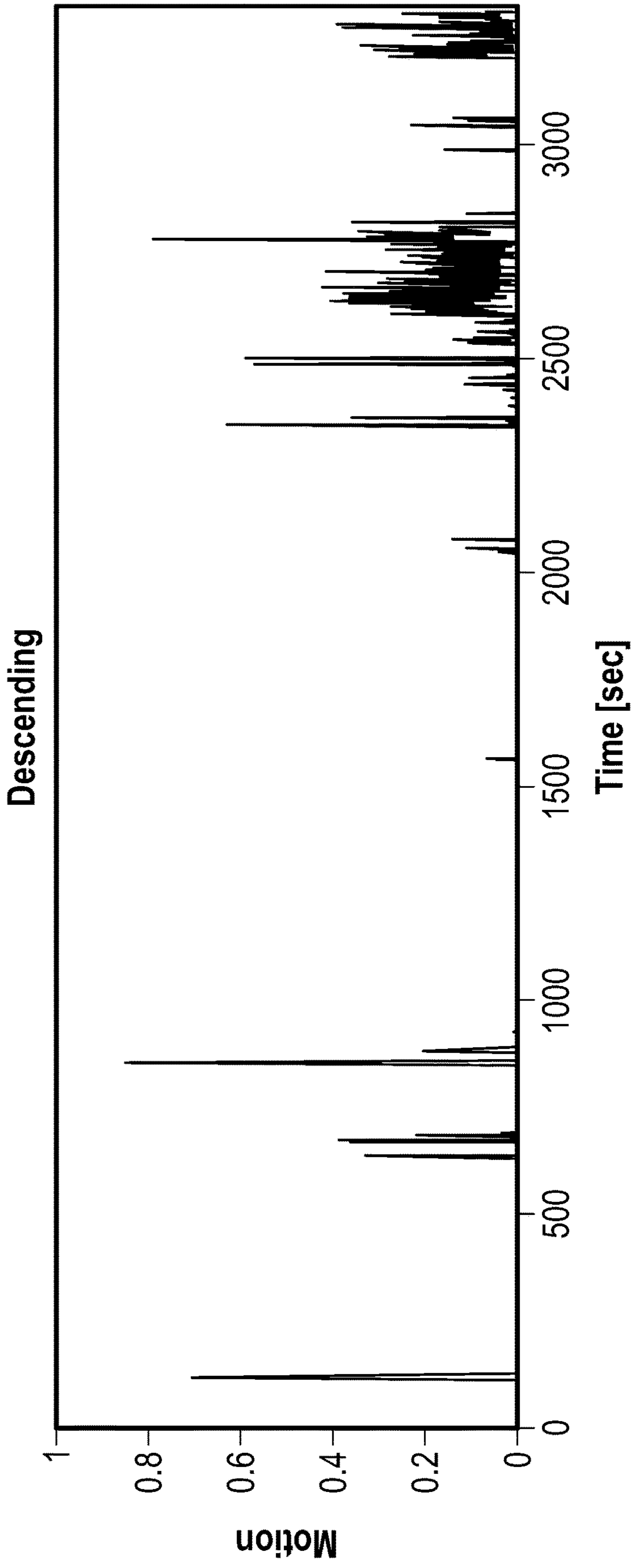
FIG. 9D is an exemplary graph of the output of the motion detector for images of a descending colon, in accordance with aspects of the disclosure.

In accordance with aspects of the present disclosure, a characteristic measure may include a motion score for an image which estimates a degree of motion that a CE imaging device (e.g., 212, FIG. 2) experienced when the CE imaging device captured the image. FIGS. 9A-9E illustrate graphs of exemplary motion scores versus time for images captured in various segments of the GIT. FIG. 9A shows a graph of the motion score versus time for the cecum portion of the GIT. In the graph, the CE device generally has a low motion score. In FIG. 9B, a graph of the motion score versus time for the ascending colon portion of the GIT is shown. In this graph, the CE device is in the ascending portion for about 2 seconds and has a relatively higher motion score of over 0.5 on average. Referring to FIG. 9C, a graph of the motion score versus time for the transverse portion of the colon, is shown. The motion score for the CE device is higher at the beginning and the end of the graph. Referring to FIG. 9D, a graph of the motion score versus time for the descending portion of the colon, is shown. This graph covers a range of approximately 3500 seconds. The motion score for this graph is highest, on average, around 2500-3000 seconds.

Figure 9E:
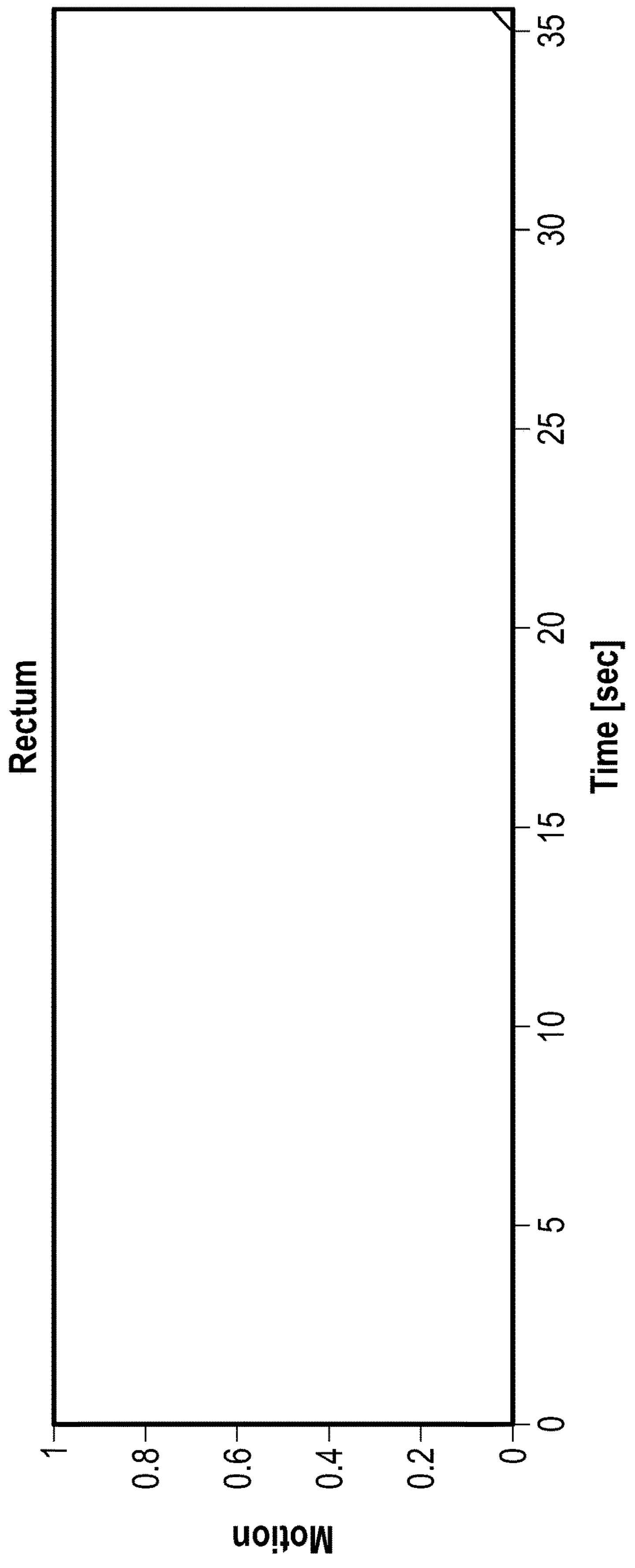
FIG. 9E is an exemplary graph of the output of the motion detector for images of a rectum, in accordance with aspects of the disclosure.

Referring to FIG. 9E, a graph of the motion score versus time for the rectum is shown. In this graph, the average motion score is almost zero. Persons skilled in the art will recognize techniques which can be used to process images to provide a motion score, such as, for example, the techniques described in U.S. Pat. No. 8,792,691, which is hereby incorporated by reference herein in its entirety. Such and other techniques are contemplated to be within the scope of the present disclosure for determining a motion score. In various embodiments, the motion score may be a characteristic measure. In various embodiments, a characteristic measure may be determined by counting the number of frames in which the motion score is above a predetermined threshold. In various embodiments, such a characteristic measure may be determined for segments of a portion of a GIT. For example, a characteristic measure may be determined based on a calculation that there were 40 frames in motion in the cecum. Such and other embodiments are contemplated to be within the scope of the present disclosure.

FIGS. 8 and 9A-E are exemplary, and other characteristic measures for determining an adequacy measure for a CE procedure are contemplated to be within the scope of the present disclosure. For example, in various embodiments, characteristic measures may include one or more of an anatomical colon segment associated with the image, a transit pattern of the capsule endoscopy device, CE device communication errors, an anatomical landmark in the plurality of images, coverage of GIT tissue in the plurality of images, a transit time, a per image indication that the image does or does not include at least one polyp, a time percentage indicating a time that the capsule endoscopy device captured the image over a time duration that the capsule endoscopy device was within a GIT portion of interest, and/or a progress percent indicating a displacement of the capsule up until each image and relative to a whole GIT portion to be imaged, among other things. Such and other embodiments are contemplated to be within the scope of the present disclosure.

Figure 10:
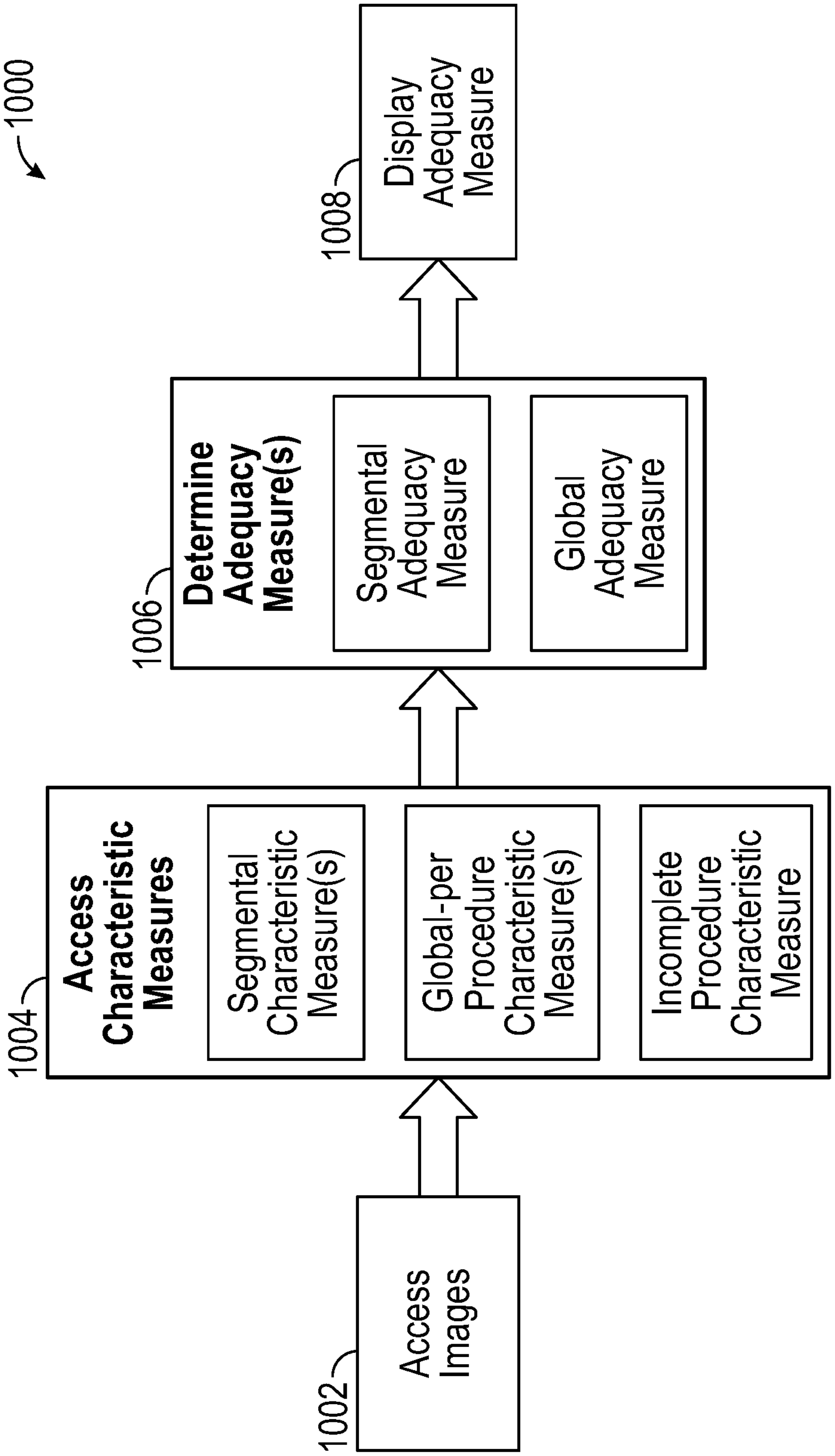
FIG. 10 is a flowchart of an exemplary method for estimating the adequacy of a capsule endoscopy procedure in accordance with aspects of the disclosure.

The flow diagram of FIG. 10 shows a computer implemented method 1000 for estimating the adequacy of a capsule endoscopy procedure. In various aspects, the images may include portions of the GIT detailed above. Persons skilled in the art will appreciate that one or more operations of the method 1000 may be performed in a different order, repeated, and/or omitted without departing from the scope of the disclosure. In some methods in accordance with this disclosure, some or all of the operations in the illustrated method 1000 can operate using a capsule endoscopy, e.g., CE imaging device 212 (see FIG. 2), the receiving device 214 (see FIG. 2), and the computing system 300 (see FIG. 2). Other variations are contemplated to be within the scope of the disclosure. The operations of FIG. 10 will be described with respect to a computing device, e.g., computing system 300 of system 200 (FIG. 2) for analyzing medical images captured in vivo via a CE procedure, or any other suitable computing system device or location thereof including a remotely-disposed computing device. It will be understood that the illustrated operations are applicable to other systems and components thereof as well.

As mentioned above, an adequacy measure for a CE procedure may provide a measure of whether the imaging coverage provided by a stream of images captured in a CE procedure was adequate to capture an event of interest (whether or not any exist). An advantage is reduction of false negatives in which a patient is incorrectly cleared of medical conditions because the steam of images did not visualize any events or indications related to the medical conditions. If the CE procedure is determined to be inadequate, the computing system 300 may recommend a repeat CE procedure or may provide information with the warning that a repeat procedure is recommended.

Initially, at block 1002, the operation includes accessing images (e.g., a time series of images) of at least a portion of the GIT (e.g., the colon 400) captured by a CE device during a CE procedure. The plurality of images may be one of: all of the images captured during the CE procedure and uploaded from the CE imaging device (and/or computing system 300) (or received), all of the images captured and received/uploaded from the computing system 300 of a GIT portion of interest (e.g., esophagus, SB, Colon, SB, and/or colon), all of the images captured and received/uploaded from the computing system 300 of a pre-defined segment of an area or portion of interest of the GIT (e.g., the transverse colon when the area of interest is the colon).

At block 1004, the operation includes accessing one or more characteristic measures associated with the images, such as one or more of the characteristic measures described above. In aspects, the characteristic measure(s) may be chosen in a clinically rational manner, which provides the advantage that the rationale for excluding certain CE procedures as inadequate will be explainable to a clinician, thus providing for a better adoption level by the users of the present technology. In aspects, the characteristics corresponding to the characteristic measure(s) may be determined based on a measured correlation between the level or existence of the characteristics and the adequacy of a procedure.

In aspects, the characteristic measure(s) may be determined based on the accessed images, as explained above, and may be, or may be based on, a motion score (FIGS. 9A-E) and/or a cleansing score (FIG. 8)). As mentioned above, a characteristic measure based on motion score may be a number of images for which the motion scores indicate that the CE device was in motion. As mentioned above, a characteristic measure based on cleansing score may be an average cleansing score per segment of the GIT. In aspects, the operation may determine an overall characteristic measure for all the segments of the GIT by averaging the cleansing score of each of the segments of the GIT.

In aspects, the characteristic measure(s) may include an anatomical colon segment in which the image was captured, a transit pattern of the capsule endoscopy device, CE device communication errors, an anatomical landmark in the plurality of images, and/or coverage of GIT tissue in the plurality of images. Persons skilled in the art will understand how to determine such characteristic measures based on the present disclosure, the references incorporated by reference into this disclosure, and/or knowledge in the art.

In aspects, an incomplete procedure characteristic measure may be based on an indication of no visualization of a colon in the plurality of images, possible visualization of a colon in the plurality of images, and/or no body exit (e.g., where the CE device does not exit the patient's body). The incomplete procedure characteristic measure may have a value of 1 or 0. In aspects, if there is retention of the CE device in the GIT, then the score may be zero. For example, in a case where the CE device did reach the colon or the captured images may only cover a portion of the colon (e.g., due to technical issues, depletion of power, etc.), the incomplete procedure characteristic measure may have a value of zero. In aspects, the incomplete procedure characteristic measure may be determined by a machine learning system.

Some of the characteristic measures may be considered to be segmental measures in that such measures are applicable to a characteristic of a segment/portion of a GIT. Some of the characteristics may be considered to be global characteristic measures in that such measures are applicable to every portion of the procedure. Some of the characteristics may relate to an incomplete procedure characteristic, which is indicative of the procedure being incomplete for any reason, as described above.

At block 1006, the operation includes determining an adequacy measure for the procedure. In various embodiments, the adequacy measure for a procedure may be based on adequacy measures for various segments of the GIT, a global-per-procedure adequacy measure, and/or the incomplete procedure characteristic measure, as described in more detail below. For now, it is sufficient to note that, in various embodiments, the adequacy measure for the procedure may be determined by multiplying a weighted segmental adequacy measure for one or more segments of a GIT, a weighted global adequacy measure, and/or a weighted incomplete procedure characteristic measure.

In aspects, each image of the plurality of images of the GIT may be associated with one segment of the plurality of consecutive segments of the GIT, such as the cecum, the ascending colon, the transverse colon, the descending colon, and/or the rectum. In aspects, the operation may determine the segmental adequacy measure for each segment of a plurality of consecutive segments of the GIT based on one or more of: a motion score, a per segment cleansing score, a transit time, a per image indication that the image does not includes at least one polyp, a time percentage indicating a time that the capsule endoscopy device captured the image over a time duration that the capsule endoscopy device was within a GIT portion of interest, and/or a progress percent indicating a displacement of the capsule up until each image and relative to a whole GIT portion to be imaged. For example, the operation may analyze each image of the plurality of images of the GIT to determine the score indicative of an average cleansing level per segment. An image may include poor cleansing. For example, the image may include large amounts of fecal matter or enough feces or dark fluid to prevent a reliable exam. In aspects, a score may be determined per segment of the GIT, and then the segmental adequacy measure may be determined based on the per segment score. In aspects, when determining the per segment score, different characteristics may be utilized for different segments. For example, for the cecum, the motion score may be used to determine a cecum segment adequacy measure, and for the ascending colon segment, a cleansing score may be used to determine the ascending colon segment adequacy measure. In aspects, the per segment adequacy measure of one segment may be multiplied by the per segment adequacy measure of a previous segment. In aspects, the segmental adequacy measure may be determined by a machine learning system.

In various embodiments, the segmental adequacy measure may be a product of multiplying at least two of: a motion score, a cleansing level per segment, and/or a transit time. Multiplication is used as an example, and any other function to combine the scores are contemplated. In aspects, a score may be determined for each segment of the GIT, and a segmental adequacy measure may be determined based on the scores per segment of the GIT. In aspects, a regional score may be used. For example, the colon may be divided into two regions (e.g., merging the first three segments, which are proximal segments, and the last two segments, which are distal segments). In aspects, a segmental probability for each segment may be based on a non-linear function of motion score or a cleansing level per segment and/or a transit time. Then, the segment adequacy measure may be based on multiplying all the segmental probabilities. In various embodiments, this multiplication may be replaced by other functions, e.g., weighted average function. The segmental adequacy measure(s) may be used in various ways to determine an adequacy measure for a procedure.

As mentioned above, the global-per procedure characteristic measure(s) may be calculated for all images and for all GIT segments that the CE device imaged. In aspects, the global adequacy measure may be based on one or more global-per procedure characteristic measures, among other things. In aspects, the global adequacy measure may be based on an average cleansing score over all of the segments, a demographic of a patient, a last segment of the GIT that the CE device reached, and/or an absolute time the CE device spent in the portion of the GIT. The demographic of the patient may include but is not limited to, for example, age, gender, BMI, weight, height, smoking, incidence of family who have had colorectal cancer, and/or nutrition. For example, the operation may utilize a lower adequacy measure threshold for a patient that is female than a patient that is male, in determining adequacy of a procedure for certain events of interest. In aspects, the global adequacy measure may be determined by a machine learning system. The global adequacy measure may be used in various ways to determine an adequacy measure for a procedure.

As described above, the adequacy measure for a procedure provides a measure of whether or not the imaging coverage provided by a stream of images captured by the CE procedure was adequate to capture an event of interest (whether or not any exist). The event of interest may include a contraction, fresh bleeding, stricture, at least one polyp (e.g., a significant polyp), and/or a disease. For example, the event may include one polyp, all polyps, and/or polyps of a specific size (e.g., 6 mm and above). The term "disease" and its derivatives, may also include syndromes (such as IBS), bowel disorders, etc. A disease may be diagnosed by indicators of a certain appearance that may appear or may be found in the images. Such and other events of interest are contemplated to be within the scope of the present disclosure.

In aspects, the adequacy measure for a procedure may be determined based on a classical machine learning technique (such as classical machine learning classifier 700, using the characteristic measures as inputs), a deep learning technique (such as deep learning classifier 500), or heuristics using the characteristic measures as inputs. For example, the classical machine learning technique may include but is not limited to an SVM and/or a decision tree. For example, the deep learning technique may include a CNN. The heuristics may include a set of rules, such as a cascade of if-then statements. In aspects, the adequacy measure for a procedure may further include a product of multiplying at least two of: the segmental adequacy measure, the global adequacy measure, and/or the incomplete procedure characteristic measure.

At block 1008, the operation includes displaying the determined adequacy measure. In accordance with aspects of the present disclosure, the adequacy measure may be presented as a value, a color, and/or a category. The value may be, for example, between 0 and 1. The color may be, but is not limited to, red/yellow/green. The categories may include, but are not limited to, adequate/inadequate and/or good/bad. In aspects, the adequacy of a CE procedure may be determined based on the adequacy measure being above a predetermined threshold level. The operation may further include providing an indication of whether or not to exclude the CE procedure, where the indication is based on the determined adequacy measure. For example, the operation may display for the clinician an indication to exclude the CE procedure. In other aspects, a procedure may be excluded automatically once it is identified as inadequate. Based on the indication to exclude, the clinician may decide to repeat the CE procedure or have the patient go for a colonoscopy. For example, the operation may display an adequacy measure of 0.25 (e.g., a value) and an indication that the CE procedure was inadequate based on such a value (e.g., if below a predetermined threshold). The operation may provide the clinician a reason why the CE procedure was excluded, such as "the transit time for the cecum is too short." Other examples may include but are not limited to: "the overall cleansing level is too low," "the capsule hasn't passed the ascending colon," and "the capsule hasn't passed the descending colon AND there were too few motion frames in the cecum AND there were too few motion frames in the ascending colon."

In aspects, the operation may provide an indication that a CE procedure is inadequate and may exclude all images from the study except for a short clip of the plurality of images that may provide the clinician the ability to determine where the capsule finished.

In aspects, the operation may exclude inadequate CE procedures. In aspects, the operation may overrule an exclusion when the CE procedure actually displays the event or a portion of the event. For example, in aspects, the operation may overrule the decision to exclude in cases where it is confident there is at least one significant polyp.

In aspects, the operation may exclude the CE procedure automatically based on the determined adequacy measure. The operation or other method or system may, in a case where the adequacy measure is below a predetermined threshold, detect the predetermined event in the plurality of images. For example, a polyp or a polyp of a pre-defined minimal size may be detected in the images provided via the procedure. Next, an event score may be received based on the detecting. A decision to overrule the procedure may be made based on the event score or based on the event score and the adequacy measure. As an example, calculating a probability score for presence of at least one polyp is addressed in co-pending U.S. patent application No. 63/075,795. The entire contents of the co-pending patent application are hereby incorporated by reference. Other techniques for calculating an event probability score will be understood by persons skilled in the art.

In aspects, a CE procedure of relatively low quality may be excluded from a study. For example, sometimes procedures may still be "adequate" according to the adequacy measure, but the quality may be very poor (e.g., significant occlusions in the images or a CE procedure that is missing a lot of images due to connectivity issues). Such procedures may be excluded even though the adequacy measure may indicate that the procedure was adequate.

Accordingly, described above is an adequacy measure for indicating a measure of whether or not the imaging coverage provided a stream of images captured by a CE procedure was adequate to capture an event of interest (whether or not such an event of interest actually exists in a patient). As mentioned above, when it is not possible to construct a three-dimensional view of the GIT or portion of the GIT of a patient, various characteristic measures (such as those described above) provide indications of whether the CE procedure was adequate. Another embodiment for determining the adequacy of a CE procedure is described below in connection with FIGS. 11-20.

Figure 11:
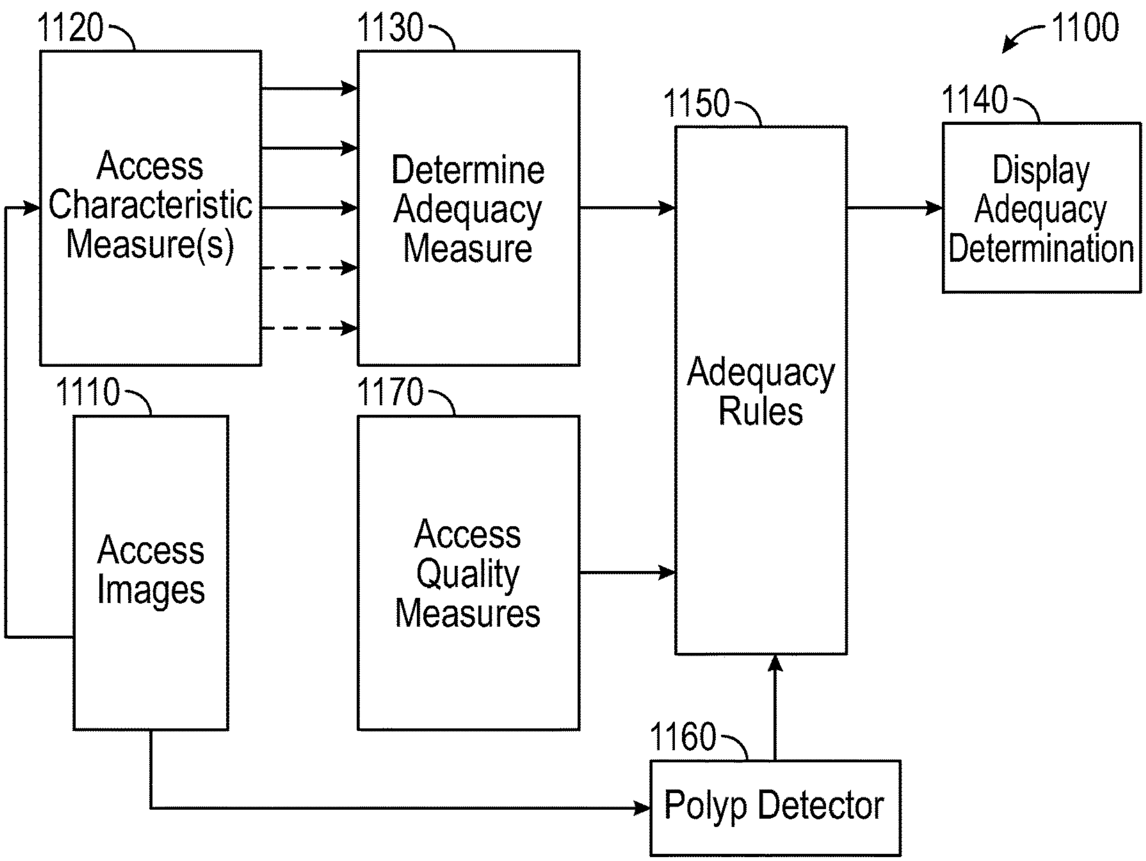
FIG. 11 is a flow diagram of another exemplary method for estimating the adequacy of a capsule endoscopy procedure, in accordance with aspects of the disclosure.

FIG. 11 shows a flow diagram of another embodiment of a computer-implemented method 1100 for estimating the adequacy of a capsule endoscopy procedure. Persons skilled in the art will appreciate that one or more operations of the method 1000 may be performed in a different order, repeated, and/or omitted without departing from the scope of the disclosure. The operations of FIG. 11 may be implemented by a computing device, e.g., computing system 300 of FIG. 2 or FIG. 3, for analyzing medical images captured in vivo via a CE procedure, or any other suitable computing system device or location thereof, including a remotely-disposed computing device. It will be understood that the illustrated operations are applicable to other systems and components thereof as well.

Initially, at block 1110, the operation includes accessing images (e.g., a time series of images) of at least a portion of the GIT (e.g., the colon 400) captured by a CE device during a CE procedure. The images accessed at block 1110 may, for example, be the images accessed at block 1002 of FIG. 10, which were described above herein.

Figure 18:
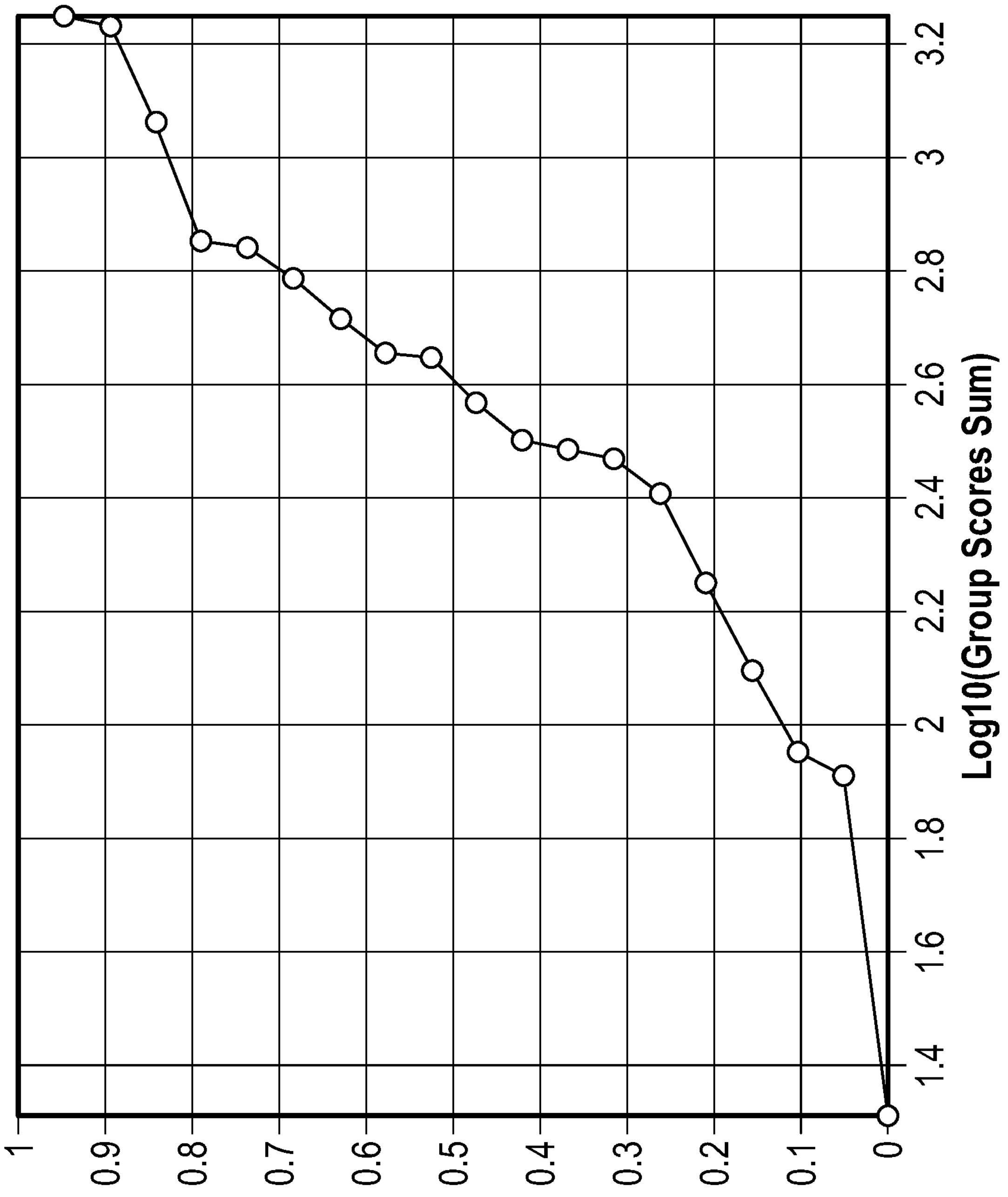
FIG. 18 is graph of an exemplary mapping, in accordance with aspects of the disclosure.

At block 1120, the operation includes accessing one or more characteristic measure(s). Various characteristic measures will be described in more detail later herein, including, for example, a characteristic measure indicative of how many images capture the same tissue region (FIG. 12), a characteristic measure indicative of a cleansing ratio (FIG. 16), and/or a characteristic measure indicative of a number of distinct views (FIG. 18). In aspects, the characteristic measures may further include demographic information for the patient undergoing the CE procedure. Demographic information may include, for example, age and/or gender.

At block 1130, the operation includes determining an adequacy measure for the CE procedure based on one or more of the characteristic measures. As described above, the adequacy measure indicates a measure of whether the imaging coverage provided by a stream of images captured by a CE procedure was adequate to capture an event of interest (whether or not any actually exist). In aspects, adequacy measure may be determined based on heuristics using the characteristic measures as inputs, by a classical machine learning technique (such as classical machine learning classifier 700, using the characteristic measures as inputs), and/or by a deep learning technique (such as deep learning classifier 500), among others. An example of determining an adequacy measure will be described in more detail later herein.

At block 1170, the operation may access quality measures which indicate the quality of the CE procedure. The quality measures may include, for example, an average cleansing score over all segments of the GIT, a demographic of a patient, a last segment of the GIT that the CE device reached, CE device communication errors, a suspected retention of the CE device in the GIT, or an absolute time the CE device spent in the portion of the GIT, among other indicators of the quality of the CE procedure and/or the captured images. For example, the quality measures may compare the time the CE device spent in the left colon vs. the time the CE device spent in the right colon. Various criteria and/or thresholds may be used in connection with the quality measures to determine whether the CE procedure and/or the captured images satisfy quality criteria. Other example quality measures may include excluding and/or warning if not more than a predetermined number of segments (e.g., three segments) were reached according to a GIT segmentation algorithm 1720 (FIG. 17), excluding and/or warning if all of a specific segment of the GIT was not reached by the CE device, and/or excluding or warning if entire GIT transit time is smaller than a predetermined period of time (e.g., about ten minutes).

For example, the time in the right and/or left colon may be a quality measure and may be determined by using a GIT segmentation algorithm, which will be described in connection with FIG. 17, to identify images which were captured in the right colon and images which were captured in the left colon. Time stamps associated with such images may be used to determine the amount of time a CE imaging device was in the right colon and/or the amount of time a CE imaging device was in the left colon. In various embodiments, if the time in the left colon and/or the time in the right colon do not meet certain thresholds, the quality measure may not be satisfied.

The average cleansing score over the GIT may be a quality measure and can be determined, for example, by accessing a cleansing score for each image, in the manner described above herein, and averaging the cleansing scores across all images. In various embodiments, if the average cleansing score over the entire GIT does not meet a certain threshold, the quality measure may not be satisfied.

Technical failures may be a quality measure and may include communication gaps, which are a way to determine if too many images are lost. For example, the operation may compare this percentage lost images to a predetermined threshold. For example, the operation may calculate the percentage of lost images out of the total images and if this percentage is greater than about 25% then the quality measure may fail. Other percentages may be used for the quality measure.

Suspected retention of a CE imaging device by the GIT may be a quality measure. The operation may determine if there is a suspected retention of the CE device in the GIT based on detected segment transitions, an indication of no visualization of a colon in the plurality of images, possible visualization of a colon in the plurality of images, and/or no body exit (e.g., where the CE device does not exit the patient's body). In aspects, if there is suspected retention of the CE device in the GIT, the quality measure may not be satisfied.

The quality measures and thresholds and conditions described above are exemplary, and other quality measures and threshold or conditions are contemplated to be within the scope of the present disclosure.

At block 1150, the operation may include applying a set of adequacy rules which consider the adequacy measure determined at block 1130, the quality measures accessed at block 1170, and the output of a polyp detector 1160. The polyp detector 1160 may process the images accessed at block 1110 and may operate to identify, with high confidence, images which contain a polyp. An example of a polyp detector 1160 is described in U.S. Patent Application No. 63/075,795, which is hereby incorporated by reference herein in its entirety.

With continuing reference to block 1150, in various embodiments, the adequacy rules may determine the adequacy of the CE procedure based on rules which will be described in connection with FIGS. 19 and 20. In various embodiments, if any of the quality measures are not satisfied, the adequacy rules may provide an indication that the procedure was inadequate, which will be described in connection with FIG. 20. In various embodiments, if the adequacy measure or the quality measures indicate that a procedure was inadequate, but the polyp detector identifies an image of at least one polyp with high confidence, the adequacy rules 1150 may determine the procedure to be inadequate with the inadequate determination overruled by the polyp detector. Such adequacy rules are exemplary, and variations are contemplated to be within the scope of the present disclosure. For example, in various embodiments, the operation of FIG. 11 may not include a polyp detector 1160 and, therefore, may not overrule the adequacy measure or the quality measures. In various embodiments, the operation of FIG. 11 may not involve quality measures. Such and other variations are contemplated to be within the scope of the present disclosure.

At block 1140, the operation includes displaying the adequacy determination. If the CE procedure is determined to be inadequate, the operation may provide one or more reasons why the procedure was inadequate. For example, reasons for determining that a procedure was inadequate may include: colon was not visualized, short transit time, poor cleansing, technical failure (such as a communication gap), right and/or left colon were not visualized, and/or right and/or left colon were only partially visualized, among other things. If the CE procedure is determined to be adequate, the operation may display for the clinician an indication that the CE procedure was adequate and is to be included in a study. In other aspects, a procedure may be excluded automatically once it is identified as inadequate. Based on the indication to exclude, the clinician may decide to repeat the CE procedure or have the patient go for a colonoscopy. The operation may provide the clinician a reason why the CE procedure was excluded. For example, "the transit time for the cecum is too short." Other examples may include but are not limited to: "the colon was not visualized (retention)," "the right colon was not visualized," and "the left colon was not visualized AND there was a short transit time AND there was a communications error."

Particular examples of characteristic measures, adequacy measures, quality measures, and adequacy rules will be described below.

Figure 12:
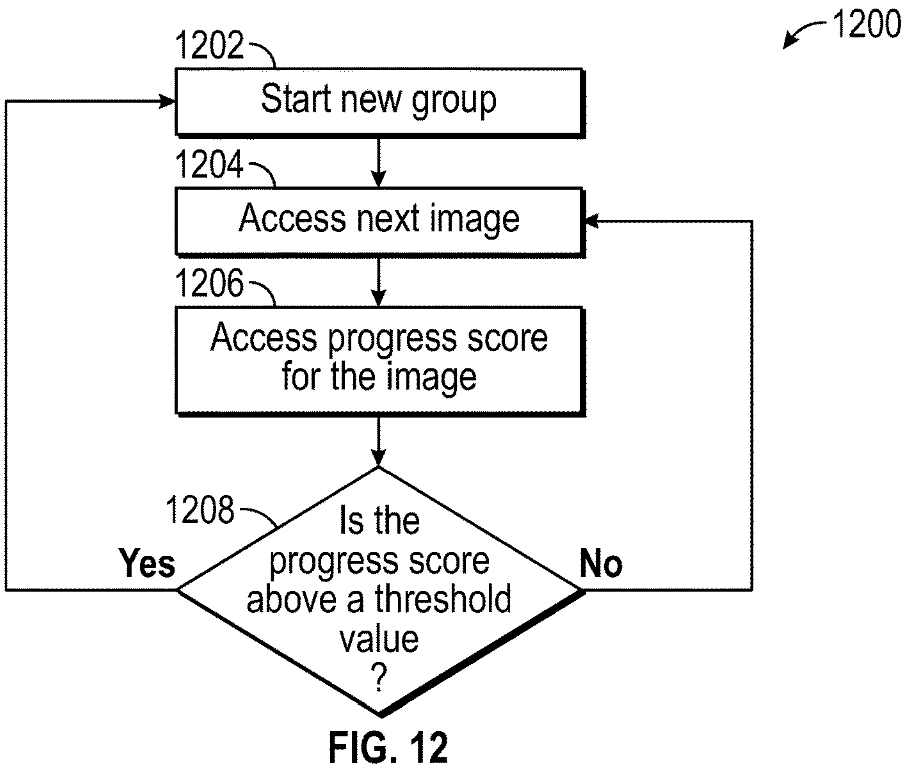
FIG. 12 is a flowchart of an exemplary method for identifying groups of images which capture the same tissue region, in accordance with aspects of the disclosure.

FIG. 12 is a flowchart of a method 1200 for providing a characteristic measure by identifying groups of images with may be captured while the CE device was static or was moving slowly and, therefore, may capture the same tissue region. The operation effectively determines a number of different "views" of a GIT based on a progress score, where each image group corresponds to a different view of the GIT.

Initially, at block 1202, the operation designates a new image group. At block 1204, the operation accesses a next image of a stream of images (e.g., a time series of images) of at least a portion of a GIT captured by a CE device during a CE procedure. At block 1206, the operation accesses a progress score for the image indicative of the movement of the CE device within the GIT when it captured the image. As mentioned above, persons skilled in the art will recognize techniques for determining a progress score, such as the techniques described in U.S. Pat. No. 8,792,691, which was incorporated by reference above.

At block 1208, the operation determines if the progress score for the image is greater than a predetermined threshold. A lower progress score can be indicative of less movement or no movement, whereas a higher progress score can be indicator of greater movement. In a case where the progress score for the image is less than or equal to a predetermined threshold, the image can be considered to capture the same view/tissue region of the GIT and can be included in the group, and the operation returns to block 1204 where a next image is accessed. If the progress score for the image is greater than the predetermined threshold, then the image can be considered to capture a different view/tissue region of the GIT and, thus, the operation can return to block 1202 and can designate the image as the start of a new group/view of the GIT. The operation of FIG. 12 continues until all images in the stream of images captured by a CE procedure have been processed. The operation of FIG. 12 is exemplary, and other techniques for identifying groups of images which may capture the same view are contemplated to be within the scope of the present disclosure.

Figure 13:
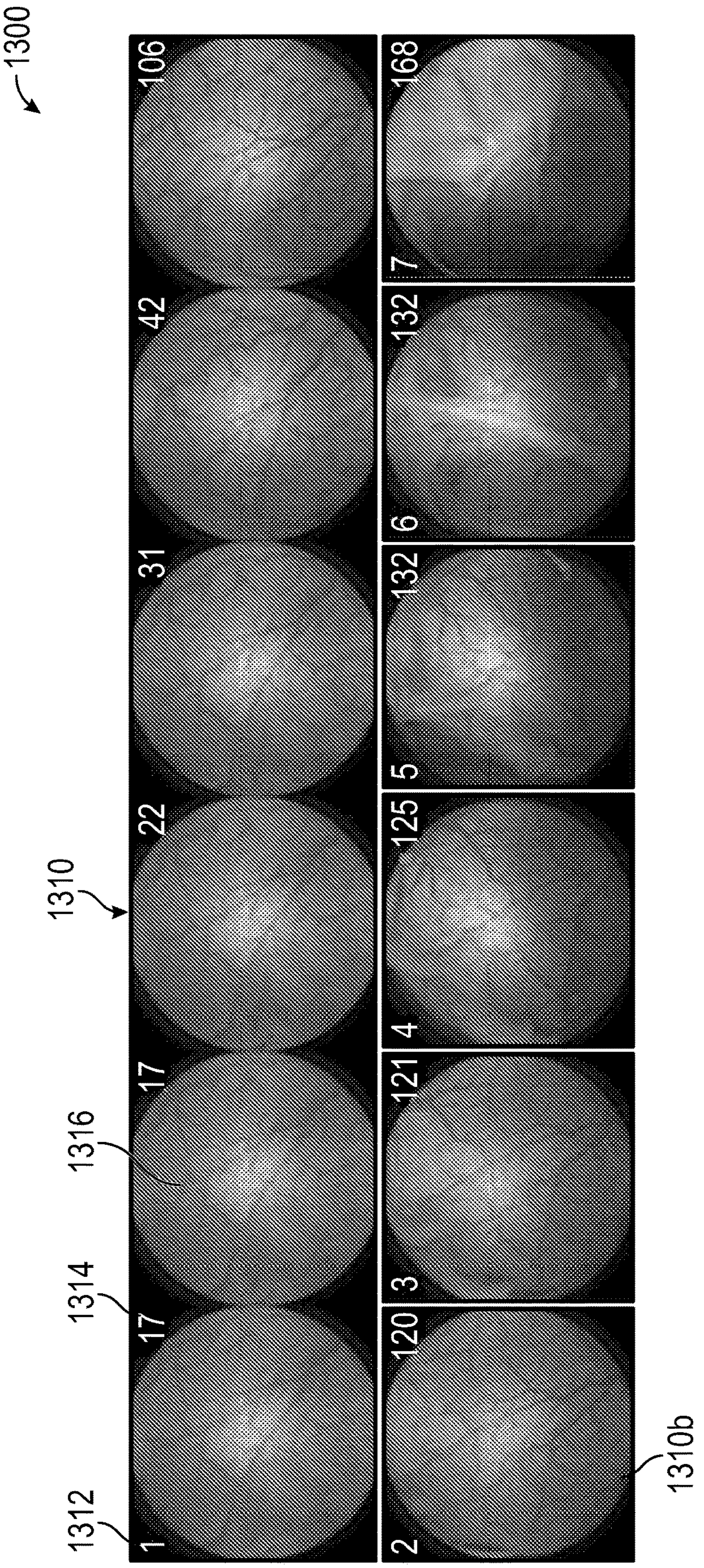
FIG. 13 is a diagram of exemplary image groups, in accordance with aspects of the disclosure.

FIG. 13 shows an example of image groups resulting from the operation of FIG. 12. FIG. 13 shows a sequence of images 1300. A first group of the images 1310 includes one or more images whose progress scores 1314 are all lower than a predetermined threshold (not shown). Thus, each group of images 1310 correspond to little or no movement within the GIT and can be considered to provide a "view" of the same tissue region. In the illustrated example, the first group 1310 includes six images 1316, which are all part of a particular group number 1312 (e.g., group "1"). Each of the images 1316 in the first group 1310 has a progress score (e.g., 1314) that is less than or equal to a predetermined threshold.

In the illustrated example, the seventh image **1310*b* has a progress score that is greater than the predetermined threshold, so it is designated as a second group. The operation of FIG. 12 continues to process the images 1300 and to group the images based on their progress scores. In the illustrated example, the twelve images 1300 were grouped into seven groups. Thus, the twelve images 1300** can be considered to provide seven different views of the GIT.

In the example of FIG. 13, the first group includes six images, whereas each of the other groups include a single image. In accordance with aspects of the present disclosure, a larger number of images of the same "view" of the GIT increases the probability of identifying an event of interest (e.g., polyp) in the particular view. Accordingly, the number of images in a group can be a characteristic measure representative of a probability of imaging an event of interest (e.g., polyp). In various embodiments, the number of images in a group can be converted to a probability of imaging an event of interest, and such a probability may be the characteristic measure. For example, in various embodiments, a group that includes a single image may have a particular probability (e.g., 15% probability) of imaging an event of interest, whereas a group that includes six images may have a much higher probability (e.g., 90% probability) of imaging an event of interest, and so on for different numbers of images in a group. The probability numbers are exemplary, and different probability numbers are contemplated to be within the scope of the present disclosure. The characteristic measures provided by FIGS. 12 and 13 can be used for generating an adequacy measure, which is described in more detail below.

Figure 14:
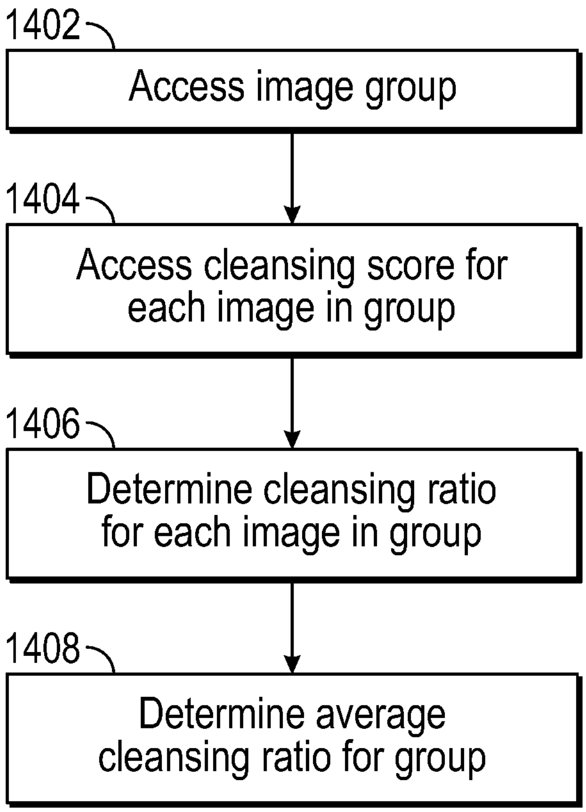
FIG. 14 is a flowchart of an exemplary method for estimating an average cleansing ratio, in accordance with aspects of the disclosure.

FIG. 14 is a flowchart of a method for providing a characteristic measure referred to herein as an average cleansing ratio. At block 1402, the operation accesses an image group determined by the operation of FIG. 12 (e.g., group 1310, FIG. 13). At block 1404, the operation accesses a cleansing score for each image in the group. As described above, persons skilled in the art will recognize how to determine a cleansing score for an image, including the techniques described in Klein A, Gizbar M, Bourke M, Ahlenstiel G. "A Validated Computerized Cleansing Score for Video Capsule Endoscopy." Dig. Endosc. 2015; 28:564-569, which was incorporated by reference above, among other techniques.

At block 1406, the operation determines a cleansing ratio for each image in the group. The cleansing ratio will be described in connection with FIGS. 15A, 15B, and 16. For example, in the first group of images 1310 of FIG. 13, each of the six images will have an associated cleansing ratio. At block 1408, the operation involves determining an average of the cleansing ratios of the images in the group. The average cleansing ratio of each group may be a characteristic measure.

Figure 15A:
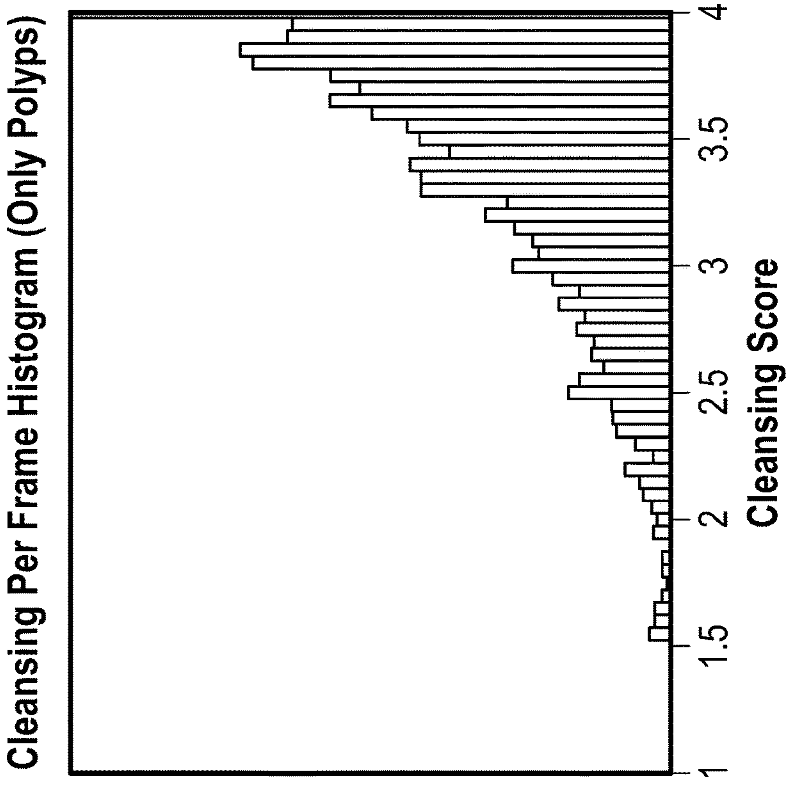
FIG. 15A is an exemplary histogram of numbers of images of polyps which have various cleansing scores, in accordance with aspects of the disclosure.
Figure 15B:
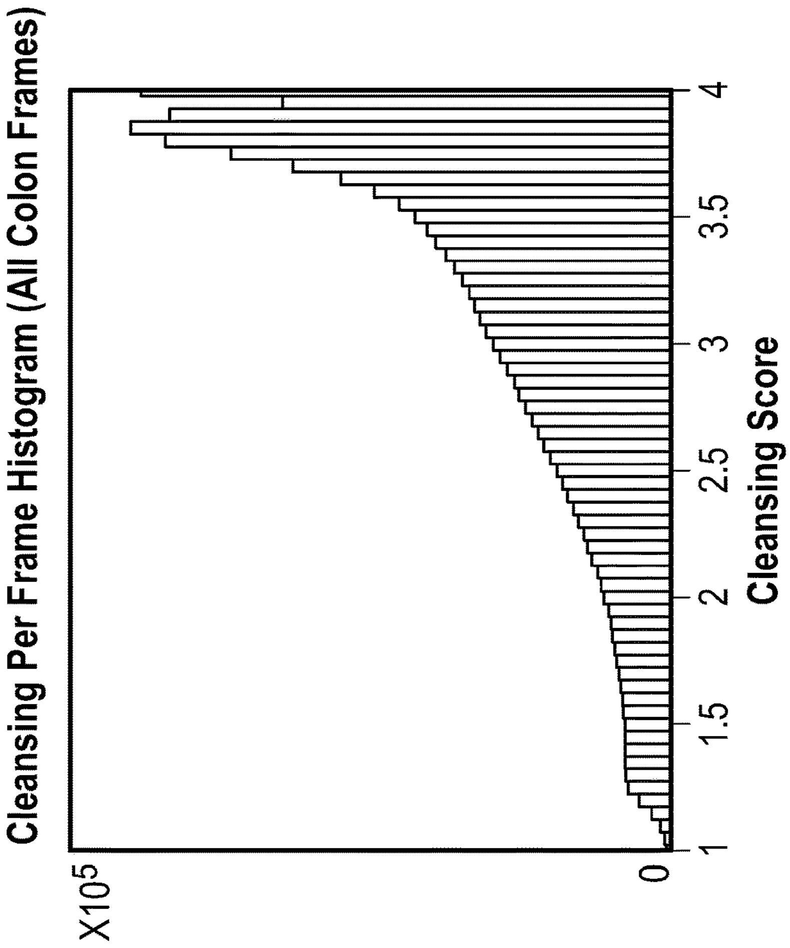
FIG. 15B is an exemplary histogram of numbers of colon images which have various cleansing scores, in accordance with aspects of the disclosure.

FIG. 15A is a histogram of number of images in a stream of images that include an event of interest (e.g., polyp) and that are tallied for each of various cleansing scores, and FIG. 15B is a histogram of number of images in the entire stream of images that are tallied for each of the various cleaning scores. In accordance with aspects of the present disclosure, the histograms of FIGS. 15A and 15B are normalized to have the same Y-axis range. In various embodiments, the Y-axis range may be a probability range of [0,1], such that FIGS. 15A and 15B may be viewed to be probability distributions. For generality, the normalized histogram of FIG. 15A will be referred to as an "event of interest histogram," and the normalized histogram of FIG. 15B will be referred to as an "all-frames histogram." The Y-axis value of each portion of the normalized histograms of FIGS. 15A and 15B will be referred to as a "normalized height." As used herein, the cleansing ratio refers to the ratio: (normalized height for a cleansing score in the event of interest histogram)/(normalized height for the cleansing score in the all-frames histogram).

Figure 16:
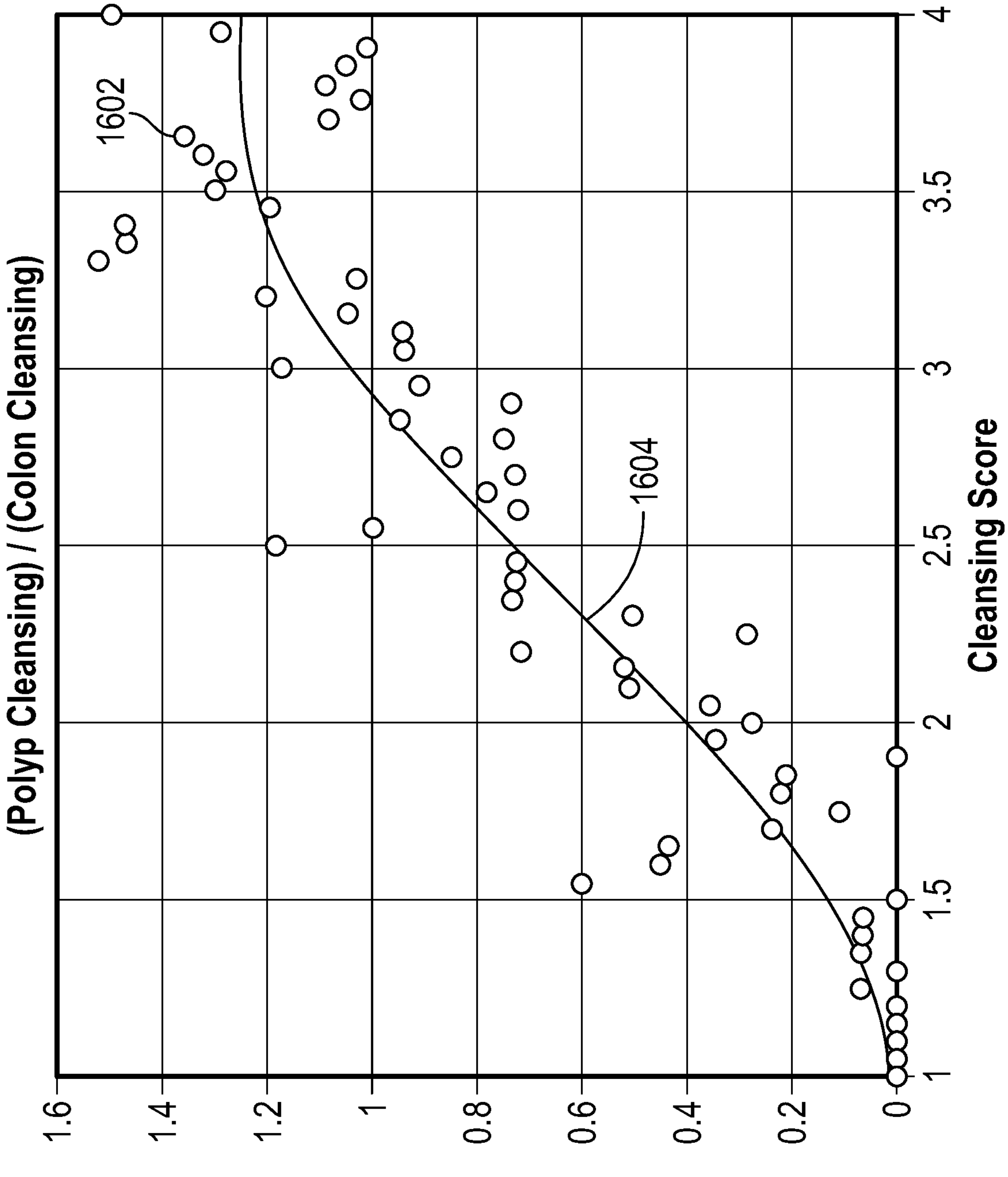
FIG. 16 is a plot of exemplary cleansing ratios based on the histograms of FIGS. 15A and 15B, in accordance with aspects of the disclosure.

FIG. 16 is a plot of the cleansing ratios 1602 across cleansing scores, where the cleansing ratios 1602 are shown by circles. In various embodiments, regression analysis can be used to fit a curve 1604 to the plotted cleansing ratios 1602 to map cleansing scores to cleansing ratios. In the illustrated example, the fitted curve 1604 is a third-degree polynomial. However, the fitted curve can be any polynomial of any degree.

In accordance with aspects of the present disclosure, the term "cleaning ratio" may refer to either the plotted cleansing ratios 1602 or may refer to the fitted cleansing ratio curve 1604. Referring also to FIG. 14, a cleansing score is accessed for each image of a group, and a cleansing ratio (e.g., 1602, 1604, FIG. 16) is determined for each image of the group based on the cleansing score. As mentioned above, the average cleansing ratio for the group may be a characteristic measure.

The illustrated embodiments of FIGS. 15A, 15B, and 16 are exemplary, and variations are contemplated to be within the scope of the present disclosure. For example, in various embodiments, separate histograms and cleansing ratio plots may be created for different portions of a GIT. For example, regarding the colon, different segments may have different behavior regarding cleansing. Generally, most images during a study come from the cecum because, during an average CE procedure, the CE imaging device spends the most time in the cecum. Separate histograms and cleansing ratio plots/fitted curves may be created for different colon segments, such as separate histograms and cleansing ratio plots/fitted curves for cecum, right or ascending colon, transverse colon, left or descending colon, and rectum. Such and other variations are contemplated to be within the scope of the present disclosure.

Accordingly, the description above relating to FIGS. 12-16 provide various characteristic measures, including a probability of imaging an event of interest (e.g., polyp) for each image group/viewpoint and an average cleansing ratio for each imaging group/viewpoint. In accordance with aspects of the present disclosure, for each image group/viewpoint, a further characteristic measure may be determined as: (probability of imaging an event of interest in the group)×(average cleansing ratio for the group), and such a measure may be referred to herein as a "group score."

In aspects of the present disclosure, the adequacy measure for the CE procedure may be the sum of all group scores for the image groups identified by the operation of FIG. 12. A higher sum of group scores may indicate that there are more multi-frame views of the GIT with acceptable cleansing, and a lower sum of group scores may indicate that there are fewer multi-frame views of the GIT and/or the cleansing was sub-optimal. In various embodiments, the sum of group scores may be mapped to a probability, as shown in the example of FIG. 18, and the probability may serve as the adequacy measure. The mapping shown in FIG. 18 is exemplary. In various embodiments, the mapping of FIG. 18 may be determined empirically from training data and/or validation data, may be fitted to data and/or extrapolated from data, or may be arbitrary based on a desired mapping.

In aspects, the mapping shown in FIG. 18 may be provided based on a receiver operating characteristics (ROC) curve. As persons skilled in the art will recognize, a ROC curve is a graph which shows the performance of a classification model at various classification thresholds. For the purpose of generating the mapping of FIG. 18, a classification model is configured to classify each sum of group scores to one of two classifications, i.e., a "positive" classification that the imaging coverage provided by the images was adequate to capture an event of interest (whether or not such an event of interest actually exists), and a "negative" classification that the imaging coverage provided by the images was not adequate to capture an event of interest (whether or not such an event of interest actually exists). When a particular threshold is used to perform the classification, the classification model will have a particular true positive rate (TPR) and a particular false positive rate (FPR). Different thresholds will yield different TPR and FPR, and in various embodiments, the different thresholds may span the entire range of possible values for the sum of group scores. As persons skilled in the art will understand, a ROC curve is generated by plotting these pairs of FPR and TPR for different thresholds in a two-axis coordinate space where the x-axis represents false positive rates (FPR) and the y-axis represents true positive rates (TPR), and then performing interpolation between the plotted coordinates or fitting a curve to the plotted coordinates. The ROC curve may be the fitted curve, or the ROC curve may be the plotted coordinates together with the interpolations between plotted coordinates, or some combination of both.

In accordance with aspects of the present disclosure, a ROC curve, for a classification model which classifies sum of group scores as adequate or inadequate, may be used to generate the mapping of FIG. 18. As mentioned above, the ROC curve is created from different threshold values, which may span the range of possible values for the sum of group scores. Thus, each threshold value may, in a way, be viewed as a proxy for a particular sum of group scores, and the true positive rate corresponding to a threshold value may be viewed as the probability that the imaging coverage provided by the images was adequate to capture an event of interest (whether or not such an event of interest actually exists). Accordingly, the mapping of FIG. 18 may be used to map a sum of group scores to a probability which may be used as an adequacy measure.

The mapping of FIG. 18 and the embodiments described in connection FIG. 18 are exemplary. Other embodiments are contemplated to be within the scope of the present disclosure. For example, as described below in connection with FIG. 17, a separate sum of group scores may be computed for different segments of a GIT, and each segment of a GIT may have a corresponding mapping like the mapping shown in FIG. 18.

Figure 17:
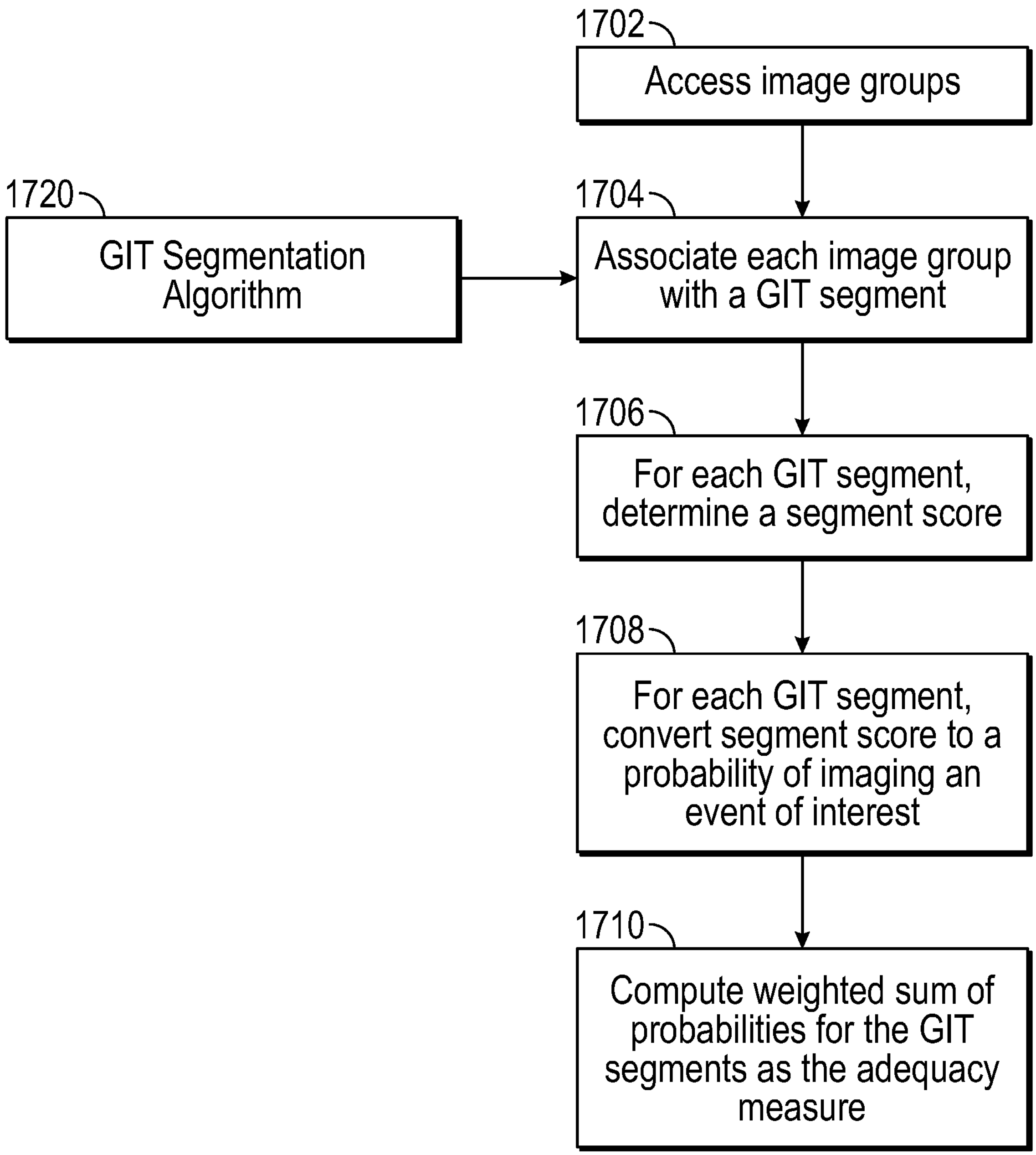
FIG. 17 is a flowchart of an exemplary method for estimating an adequacy measure for a capsule endoscopy procedure based on multiple segment scores, in accordance with aspects of the disclosure.

FIG. 17 addresses an embodiment of determining an adequacy measure when the image groups span different GIT portions, such as different portions of a colon (e.g., cecum, right or ascending colon, transverse colon, left or descending colon, and rectum). For convenience, the following paragraphs may be described with reference to colon portions. However, it is intended for the following description to apply to other GIT portions as well.

FIG. 17 is a flowchart of a method for providing an adequacy measure when multiple GIT segments are present. The operation of FIG. 17 may be performed by a computing system, such as the computing system 300 of FIGS. 2 and 3. At block 1702, the operation accesses the image groups determined by the operation of FIG. 12. At block 1704, the operation associates each image group with a GIT segment based on input from a GIT segmentation algorithm 1720, which divides a stream of images to correspond with portions of a GIT in which the images were captured. In general, the GIT segmentation algorithm 1720 may be performed, for example, based on the identification of various landmarks or transition indicators between different anatomical segments. Such identification may be performed, for example, based on machine learning techniques. One way to segment a stream of images to correspond with anatomical segments is described in U.S. patent application Ser. No. 17/244,988, which is hereby incorporated by reference herein in its entirety.

At block 1706, the operation determines a segment score for each GIT segment (e.g., the cecum, the ascending colon, etc.). The segment score for each GIT segment may be, for the example, the sum of group scores described above herein, where only image groups which are part of the GIT segment are used for the sum of group scores.

At block 1708, the operation converts each segment score to a mapped probability corresponding to the sum of group scores, which was described above in connection with FIG. 18. Each segment of the GIT may have a separate mapping like that shown in FIG. 18, which may be generated using a ROC curve for each segment. In such an embodiment, each GIT segment would have a corresponding probability, which may be interpreted as a probability that the imaging coverage of a GIT segment provided by the images corresponding to that GIT segment was adequate to capture an event of interest (e.g., at least one polyp or significant polyp) in that GIT segment, whether or not such an event of interest actually exists in a patient. For example, the probabilities for colon segments (cecum, right or ascending colon, transverse colon, left or descending colon, and rectum) may be $[P_1, \ldots, P_5]$, and such probabilities may be the result of block 1708.

At block 1710, the operation involves determining an adequacy measure for the CE procedure as a weighted sum of the probabilities for the GIT segments. For example, if the probabilities for colon segments (cecum, right or ascending colon, transverse colon, left or descending colon, and rectum) are $[P_1, \ldots, P_5]$, the weighted sum would be $$\sum_{i=1}^{5}(w_i \cdot P_i).$$

In various embodiments, the weights $[w_1, \ldots, w_5]$ may have values that are determined based on a priori probabilities of an event of interest being located in each segment. In various embodiments, the a priori probabilities may be determined empirically by compiling known instances of an event of interest (e.g., polyp) across a patient population and where they occur in the GIT in the patient population. The percentage of all instances which occur in each segment of the GIT may be determined, and such percentages may be used as a priori probabilities for the occurrence of an event of interest in the segments of a GIT. Using a numerical example for a colon, assuming the following values are determined:

| | Cecum | Ascending | Transverse | Descending | Rectum |
|---|---|---|---|---|---|
| a priori | 0.08 | 0.22 | 0.16 | 0.38 | 0.16 |
| adequacy | 0.9 | 0.8 | 0.7 | 1.0 | 0.0 |

The adequacy measure for the CE procedure may be computed as the weighted sum:

$$(0.9*0.08)+(0.8*0.22)+(0.7*0.16)+(1.0*0.38)+(0.0*0.16)=0.74$$

The particular values of the example above are illustrative, and other values are contemplated to be within the scope of the present disclosure.

In various embodiments, separate adequacy measures may be computed for separate portions of the GIT using the a priori probabilities. Continuing with the colon as an example, separate adequacy measures may be computed for a left side of a colon (e.g., descending-sigmoid colon and rectum) and for a right side of the colon (e.g., cecum, ascending colon, and transverse). In accordance with aspects of the present disclosure, the a priori probabilities for the left side of the colon may be re-normalized to 1, such that 0.38 for descending-sigmoid and 0.16 for rectum become approximately 0.7 for descending-sigmoid and 0.3 for rectum. An adequacy measure for the left side of the colon may be computed as (1.0*0.7)+(0.0*0.16)=0.7. Similarly, the a priori probabilities for the right side of the colon may be re-normalized to 1, such that 0.08 for cecum, 0.22 for ascending colon, and 0.16 for transverse become approximately 0.17 for cecum, 0.48 for ascending colon, and 0.35 for transverse. An adequacy measure for the right side of the colon may be computed as (0.9*0.17)+(0.8*0.48)+(0.7*0.35)=0.782. The colon is used merely as an example, and the disclosed technique may be applied to other portions of a GIT to determine adequacy measures for different portions of a GIT using a priori probabilities. In case a CE procedure is determined to be inadequate, the adequacy measures for different portions of a GIT may be used to explain which portion of a GIT may have caused the CE procedure to be inadequate.

Accordingly, the description above provides examples of various characteristic measures and various ways to compute an adequacy measure based on such characteristic measures. FIGS. 19 and 20 graphically illustrate examples of adequacy rules (1150, FIG. 11), which may be applied based on the adequacy measure 1130, quality measures 1170, and output of a polyp detector 1160. For convenience, the embodiments of FIGS. 19 and 20 refer to the adequacy measure as an adequacy probability, which may be a probability that is output by block 1710 of FIG. 17 or may be a probability that is mapped by FIG. 18, among other possibilities. In accordance with aspects of the present disclosure, the graph of FIG. 19 may be applied when all quality measures are satisfied, and the graph of FIG. 20 may be applied whenever any quality measure is not satisfied.

Figure 19:
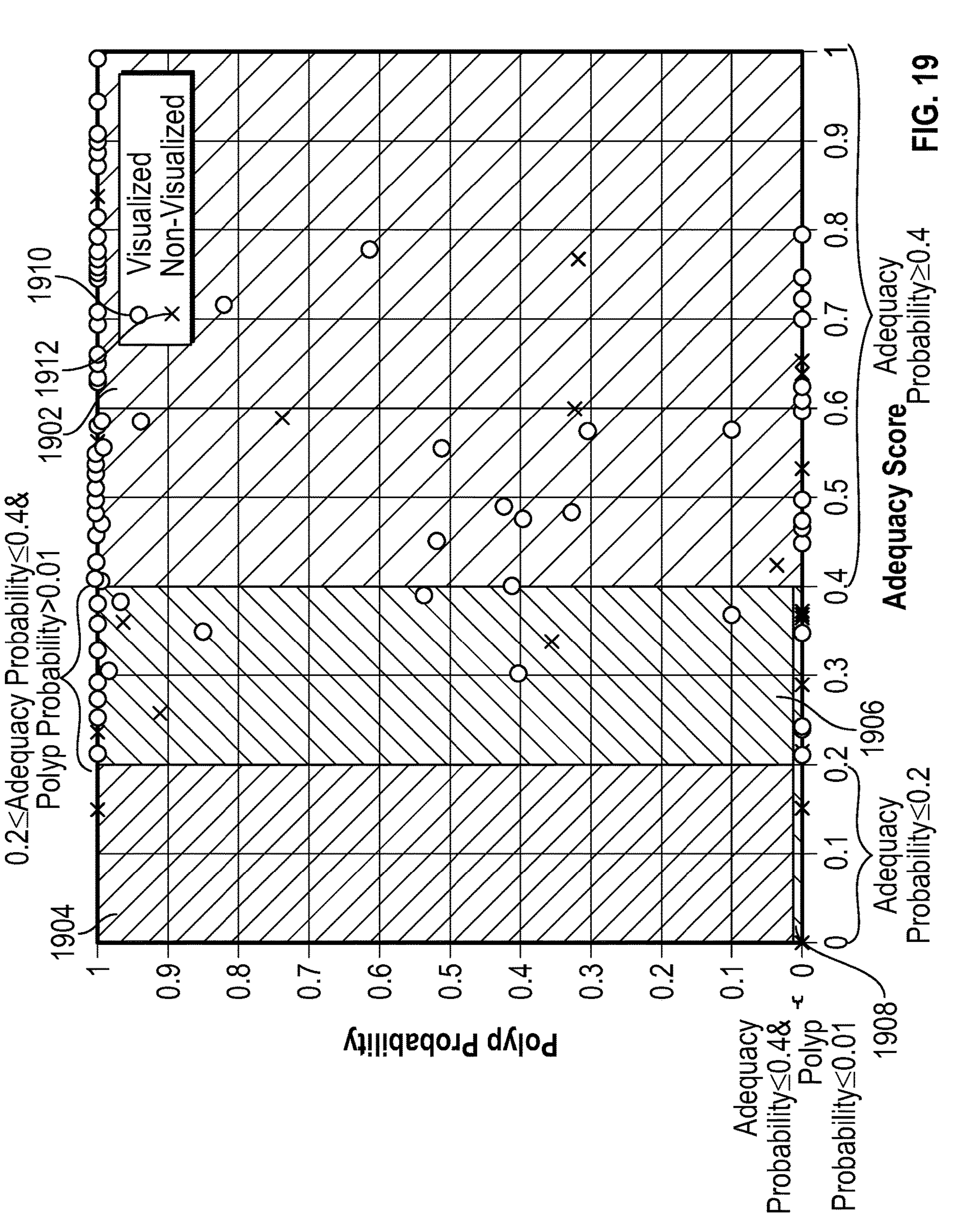
FIG. 19 is a graph depicting exemplary adequacy rules for categorizing a procedure, in accordance with aspects of the disclosure.

Referring to FIG. 19, the illustrated graph depicts combinations of polyp probability values (e.g., 1160, FIG. 11) and adequacy probability values (e.g., 1130, FIG. 11) used by the adequacy rules to categorize a CE procedure as adequate, inadequate, or inadequate but overruled, when all quality measures (e.g., 1170, FIG. 11) are satisfied. Each "O" 1910 is a plot of a CE procedure's adequacy probability and polyp probability where at least one polyp was visualized by the CE procedure. Each "x" 1912 is a plot of a CE procedure's adequacy probability and polyp probability where the CE procedure did not visualize at least one polyp. In the illustrated example, if the adequacy probability is less than or equal to 0.2 (region 1904), or if the adequacy probability is less than or equal to 0.4 and the polyp probability is less than or equal to 0.01 (region 1908), then the operation indicates that the CE procedure was inadequate. If the adequacy probability is in the range of 0.4 to 1.0 (region 1902), then the operation indicates that the CE procedure was adequate. If the adequacy measure is in the range of 0.2 to 0.4 and the polyp probability is greater than 0.01 (region 1906), then the operation indicates that the CE procedure was inadequate but overruled, which indicates that the CE procedure is inadequate based on the adequacy probability, but the inadequacy determination is overruled based on the polyp probability. Accordingly, the operation may overrule the decision to exclude the results of a CE procedure in cases where it is confident, based on the polyp probability, that there is at least one significant polyp. As described above, the operation may further display a rationale to the clinician as to why the inadequate result was overruled. As shown by the "O" and "X" markers in the graph, some of the decisions to categorize a CE procedure may not be consistent with what actually occurred in the CE procedure, such as certain markers in regions 1906 and 1902, but most of the categorizations are correct. Because it would be impractical to manually review all images of a CE procedure to identify events of interest, the adequacy determination may improve a physician's confidence in the results of a CE procedure.

The regions 1902-1908 and values shown in FIG. 19 are exemplary, and variations are contemplated to be within the scope of the present disclosure. For example, each region may be defined by a lower threshold and an upper threshold for adequacy probability and/or a lower threshold and upper threshold for polyp probability. Such lower and upper thresholds may have values different from those shown in FIG. 19. Such and other variations are contemplated to be within the scope of the present disclosure.

Figure 20:
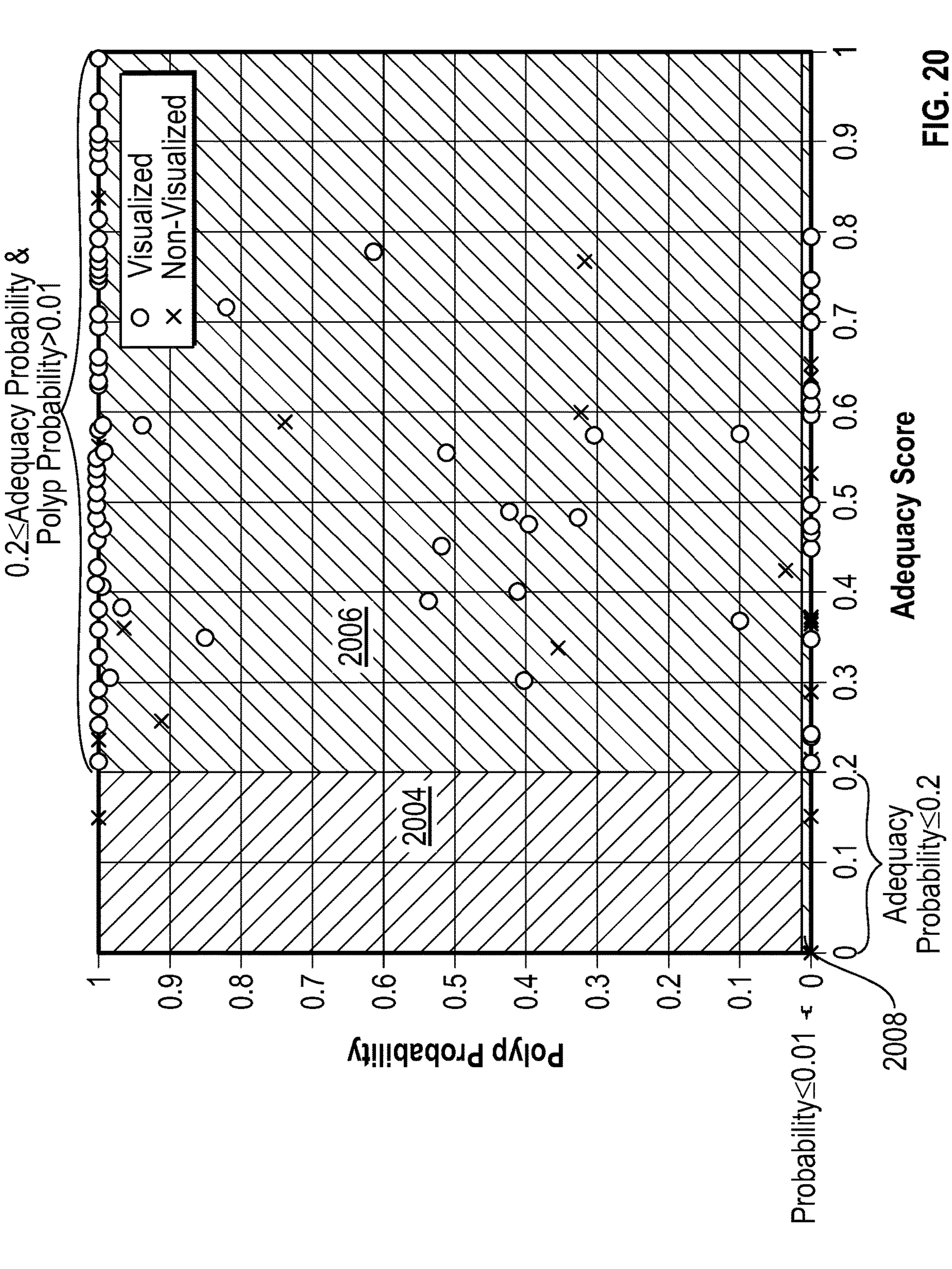
FIG. 20 is a graph depicting another set of exemplary rules for categorizing a procedure, in accordance with aspects of the disclosure.

FIG. 20 is a graph illustrating combinations of polyp probability values (e.g., 1160, FIG. 11) and adequacy probability values (e.g., 1130, FIG. 11) used by the adequacy rules to categorize a CE procedure as adequate, inadequate, or inadequate but overruled, when any quality measure (e.g., 1170, FIG. 11) is not satisfied. In the illustrated example, if the adequacy probability is less than or equal to 0.2 (region 2004), or if the polyp probability is less than or equal to 0.01 (region 2008), then the operation indicates that the CE procedure was inadequate. If the adequacy measure is in the range of 0.2 to 1 and the polyp probability is greater than 0.01 (region 2006), then the operation indicates that the CE procedure was inadequate but overruled, which indicates that the CE procedure is inadequate based on the adequacy probability, but the inadequacy determination is overruled based on the polyp probability.

The regions 2004-2008 and values shown in FIG. 20 are exemplary, and variations are contemplated to be within the scope of the present disclosure. For example, each region may be defined by a lower threshold and an upper threshold for adequacy probability and/or a lower threshold and upper threshold for polyp probability. Such lower and upper thresholds may have values different from those shown in FIG. 20. Such and other variations are contemplated to be within the scope of the present disclosure.

In various embodiments, rather than having one set of adequacy rules when all quality measures are satisfied (e.g., FIG. 19) and one set of adequacy rules when any quality measure is not satisfied (e.g., FIG. 20), more than two sets of adequacy rules may be used. For example, different adequacy rules may be used if particular quality measures are not satisfied. Such and other variations are contemplated to be within the scope of the present disclosure.

Even though the examples are shown and described with respect to images captured in vivo by a CE device, the disclosed technology can be applied to images captured by other devices or mechanisms.

The embodiments disclosed herein are examples of the disclosure and may be embodied in various forms. For instance, although certain embodiments herein are described as separate embodiments, each of the embodiments herein may be combined with one or more of the other embodiments herein. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

The phrases "in an embodiment," "in embodiments," "in various embodiments," "in some embodiments," or "in other embodiments" may each refer to one or more of the same or different embodiments in accordance with the present disclosure. A phrase in the form "A or B" means "(A), (B), or (A and B)." A phrase in the form "at least one of A, B, or C" means "(A); (B); (C); (A and B); (A and C); (B and C); or (A, B, and C)."

Any of the herein described operations, methods, programs, algorithms, or codes may be converted to, or expressed in, a programming language or computer program embodied on a computer or machine readable medium. The terms "programming language" and "computer program," as used herein, each include any language used to specify instructions to a computer, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, Python, scripting languages, Visual Basic, metalanguages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

It should be understood that the foregoing description is only illustrative of the present disclosure. To the extent consistent, any or all of the aspects detailed herein may be used in conjunction with any or all of the other aspects detailed herein. Various alternatives and modifications can be devised by those skilled in the art without departing from the disclosure. Accordingly, the present disclosure is intended to embrace all such alternatives, modifications, and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A computer-implemented method for estimating adequacy of a capsule endoscopy (CE) procedure, comprising:

accessing a plurality of images of at least a segment of a gastrointestinal tract (GIT) captured by a CE imaging device during a CE procedure;

accessing a plurality of characteristic measures associated with the plurality of images;

determining an adequacy measure for the CE procedure based on the plurality of characteristic measures, the adequacy measure indicating a measure of whether an imaging coverage captured by the plurality of images was adequate to capture an event of interest in the at least the segment of the GIT, whether or not such an event of interest actually exists in the at least the segment of the GIT; and displaying an adequacy indication for the CE procedure based on the adequacy measure, wherein determining the adequacy measure for the CE procedure is based on at least one of a classical machine learning technique, a deep learning technique, or a heuristic, wherein the at least the segment of the GIT includes a plurality of segments, wherein determining the adequacy measure for the CE procedure includes:

determining an adequacy measure for each segment of the plurality of segments, and determining the adequacy measure for the CE procedure based on the adequacy measure for each segment of the plurality of segments, wherein determining the adequacy measure for the CE procedure based on the adequacy measure for each segment of the plurality of segments includes:

accessing a priori probabilities of occurrences of the event of interest in each segment of the plurality of segments, the a priori probabilities being empirically determined based on a patient population, and determining the adequacy measure for the CE procedure based on the a priori probabilities and based on the adequacy measure for each segment of the plurality of segments.

2. The computer-implemented method of claim 1, further comprising processing the plurality of images to identify a plurality of image groups, wherein in each image group of the plurality of image groups, each image of a respective image group captures a same tissue region.

3. The computer-implemented method of claim 2, wherein a characteristic measure among the plurality of characteristic measures includes, for each image group of the plurality of image groups, a number of images in the respective image group, wherein the adequacy measure for the CE procedure is determined based on the number of images in each image group of the plurality of image groups.

4. The computer-implemented method of claim 2, wherein a characteristic measure among the plurality of characteristic measures includes, for each image group of the plurality of image groups, an average cleansing ratio for the respective image group, wherein the adequacy measure for the CE procedure is determined based on the average cleansing ratio of each image group of the plurality of image groups.

5. The computer-implemented method of claim 1, further comprising:

determining that the adequacy measure indicates that the imaging coverage provided by the plurality of images was not adequate to capture an event of interest in the at least the segment of the GIT, whether or not such an event of interest actually exists in the at least the segment of the GIT, wherein the adequacy indication for the CE procedure includes at least one reason why the CE procedure was determined to be not adequate.

6. The computer-implemented method of claim 1, further comprising:

accessing at least one quality measure associated with the plurality of images;

determining the adequacy indication based on a first set of adequacy rules when the at least one quality measure is satisfied; and determining the adequacy measure based on a second set of adequacy rules when any of the at least one quality measure is not satisfied.

7. A system for estimating adequacy of a capsule endoscopy (CE) procedure, the system comprising:

a display device;

at least one processor; and at least one memory including instructions stored thereon which, when executed by the at least one processor, cause the system to:

access a plurality of images of at least a segment of a gastrointestinal tract (GIT) captured by a CE imaging device during a CE procedure;

access a plurality of characteristic measures associated with the plurality of images;

determine an adequacy measure for the CE procedure based on the plurality of characteristic measures, the adequacy measure indicating a measure of whether an imaging coverage captured by the plurality of images was adequate to capture an event of interest in the at least the segment of the GIT, whether or not such an event of interest actually exists in the at least the segment of the GIT; and display, on the display device, an adequacy indication for the CE procedure based on the adequacy measure, wherein determining the adequacy measure for the CE procedure is based on at least one of a classical machine learning technique, a deep learning technique, or a heuristic, wherein the at least the segment of the GIT includes a plurality of segments, wherein determining the adequacy measure for the CE procedure includes:

determining an adequacy measure for each segment of the plurality of segments, and determining the adequacy measure for the CE procedure based on the adequacy measure for each segment of the plurality of segments, wherein in determining the adequacy measure for the CE procedure based on the adequacy measure for each segment of the plurality of segments, the instructions, when executed by the at least one processor, cause the system to:

access a priori probabilities of occurrences of the event of interest in each segment of the plurality of segments, the a priori probabilities being empirically determined based on a patient population, and determine the adequacy measure for the CE procedure based on the a priori probabilities and based on the adequacy measure for each segment of the plurality of segments.

8. The system of claim 7, wherein the instructions, when executed by the at least one processor, further cause the system to process the plurality of images to identify a plurality of image groups, wherein in each image group of the plurality of image groups, each image of a respective image group captures a same tissue region.

9. The system of claim 8, wherein a characteristic measure among the plurality of characteristic measures includes, for each image group of the plurality of image groups, a number of images in the respective image group, wherein the adequacy measure for the CE procedure is determined based on the number of images in each image group of the plurality of image groups.

10. The system of claim 8, wherein a characteristic measure among the plurality of characteristic measures includes, for each image group of the plurality of image groups, an average cleansing ratio for the respective image group, wherein the adequacy measure for the CE procedure is determined based on the average cleansing ratio of each image group of the plurality of image groups.

11. The system of claim 10, wherein the instructions, when executed by the at least one processor, further cause the system to determine the average cleansing ratio for each image group by:

accessing a mapping of cleansing scores to cleansing ratios; and for each image group of the plurality of image groups:

accessing a cleansing score for each image in the respective image group, determining a cleansing ratio for each image in the respective image group based on the mapping of cleansing scores to cleansing ratios, and determining the average cleansing ratio for the respective image group as an average of the cleansing ratios for the images in the respective image group.

12. The system of claim 7, wherein the instructions, when executed by the at least one processor, further cause the system to:

access at least one quality measure associated with the plurality of images;

determine the adequacy indication based on a first set of adequacy rules when the at least one quality measure is satisfied; and determine the adequacy measure based on a second set of adequacy rules when any of the at least one quality measure is not satisfied.

13. The system of claim 7, wherein the instructions, when executed by the at least one processor, further cause the system to:

determine that the adequacy measure indicates that the imaging coverage provided by the plurality of images was not adequate to capture an event of interest in the at least the segment of the GIT, whether or not such an event of interest actually exists in the at least the segment of the GIT, wherein the adequacy indication for the CE procedure includes at least one reason why the CE procedure was determined to be not adequate.

14. The system of claim 7, wherein the event of interest is appearance of a significant polyp, wherein the instructions, when executed by the at least one processor, further cause the system to:

determine that the adequacy measure indicates that the imaging coverage captured by the plurality of images was not adequate to capture an event of interest in the at least the segment of the GIT, whether or not such an event of interest actually exists in the at least the segment of the GIT; and determine that a significant polyp was detected in the plurality of images by a polyp detector which processed the plurality of images, wherein the adequacy indication for the CE procedure includes an indication that the CE procedure was determined to be not adequate but that the determination was overruled by a polyp detector.

15. A non-transitory computer-readable medium storing instructions which, when executed by a processor, cause performance of a method comprising:

accessing a plurality of images of at least a segment of a gastrointestinal tract (GIT) captured by a CE imaging device during a CE procedure;

accessing a plurality of characteristic measures associated with the plurality of images;

determining an adequacy measure for the CE procedure based on the plurality of characteristic measures, the adequacy measure indicating a measure of whether an imaging coverage captured by the plurality of images was adequate to capture an event of interest in the at least the segment of the GIT, whether or not such an event of interest actually exists in the at least the segment of the GIT; and displaying an adequacy indication for the CE procedure based on the adequacy measure, wherein determining the adequacy measure for the CE procedure is based on at least one of a classical machine learning technique, a deep learning technique, or a heuristic, wherein the at least the segment of the GIT includes a plurality of segments, wherein determining the adequacy measure for the CE procedure includes:

determining an adequacy measure for each segment of the plurality of segments, and determining the adequacy measure for the CE procedure based on the adequacy measure for each segment of the plurality of segments, wherein determining the adequacy measure for the CE procedure based on the adequacy measure for each segment of the plurality of segments includes:

accessing a priori probabilities of occurrences of the event of interest in each segment of the plurality of segments, the a priori probabilities being empirically determined based on a patient population, and determining the adequacy measure for the CE procedure based on the a priori probabilities and based on the adequacy measure for each segment of the plurality of segments.

16. The non-transitory computer-readable medium of claim 15, wherein the instructions, when executed by the processor, cause further performance of the method comprising:

accessing at least one quality measure associated with the plurality of images;

determining the adequacy indication based on a first set of adequacy rules when the at least one quality measure is satisfied; and determining the adequacy measure based on a second set of adequacy rules when any of the at least one quality measure is not satisfied.

* * * * *